(12) United States Patent
Asturias Ortega et al.

(10) Patent No.: US 8,697,083 B2
(45) Date of Patent: Apr. 15, 2014

(54) **HYPOALLERGENIC CHIMERIC PROTEINS BELONGING TO THE LIPID TRANSFER FAMILY OF *PARIETARIA JUDAICA* FOR USE IN THE TREATMENT OF ALLERGIES**

(75) Inventors: Juan Andres Asturias Ortega, Getxo (ES); Alberto Martinez Garate, Santurce (ES); Roberto Gonzales Rioja, Barakaldo (ES)

(73) Assignee: Bial Industrial Farmaceutica, S.A. (ES)

( * ) Notice: Subject to any disclaimer, the term of this patent is extended or adjusted under 35 U.S.C. 154(b) by 854 days.

(21) Appl. No.: 12/296,260

(22) PCT Filed: Apr. 11, 2007

(86) PCT No.: PCT/IB2007/001025
§ 371 (c)(1),
(2), (4) Date: Oct. 6, 2008

(87) PCT Pub. No.: WO2007/116316
PCT Pub. Date: Oct. 18, 2007

(65) Prior Publication Data
US 2009/0304727 A1    Dec. 10, 2009

(30) Foreign Application Priority Data

Apr. 12, 2006  (ES) .................................. 200600955

(51) Int. Cl.
| | |
|---|---|
| *A61K 39/00* | (2006.01) |
| *A61K 38/00* | (2006.01) |
| *A61K 39/35* | (2006.01) |
| *A61K 39/36* | (2006.01) |
| *C12N 15/09* | (2006.01) |
| *C07K 1/00* | (2006.01) |
| *C07K 14/00* | (2006.01) |
| *C07K 16/00* | (2006.01) |
| *C07K 17/00* | (2006.01) |
| *C08H 1/00* | (2006.01) |

(52) U.S. Cl.
USPC ........................................................ 424/185.1

(58) Field of Classification Search
None
See application file for complete search history.

(56) References Cited

U.S. PATENT DOCUMENTS

| | | | | |
|---|---|---|---|---|
| 7,265,208 B2 * | 9/2007 | Saxon et al. | ............... | 530/387.1 |
| 2006/0263391 A1 | 11/2006 | Mothes et al. | | |
| 2008/0286311 A1 | 11/2008 | Westritschnig et al. | | |
| 2009/0148466 A1 | 6/2009 | Mothes et al. | | |

FOREIGN PATENT DOCUMENTS

| | | |
|---|---|---|
| EP | 1219301 | 7/2002 |
| EP | 1 440 979 A1 | 7/2004 |
| WO | WO 2005/085278 * | 9/2005 |
| WO | WO 2005/085278 A1 * | 9/2005 |
| WO | WO-2005085278 | 9/2005 |
| WO | WO 2006/058359 A2 | 6/2006 |
| WO | WO-2006058359 | 6/2006 |

OTHER PUBLICATIONS

Bonura et al (Int Arch Allergy Immunol 2007, 142: 274-284, Online Feb. 22, 2006).*
Bowie et al. (Science, 1990, 257:1306-1310).*
Greenspan et al. (Nature Biotechnology 17: 936-937, 1999).*
Akdis et al., "Mechanisms of Allergen-Specific Immunotherapy" Allergy, 2000, vol. 55, pp. 522-530.
Akdis et al., "Mechanism of IL-10-Induced T Cell Inactivation in Allergic Inflammation and Normal Response to Allergens" Int. Arch. Allergy Immunol, 2001, vol. 124, pp. 180-182.
Allam et al., "Charaterization of Dendritic Cells from Human Oral Mucosa: A new Langerhans' Cell Type with high Constitutive FcεRI Expression" J Allergy Clin Immunol, 2003, vol. 112, No. 1, 141-148.
Amoresano et al., "Assignment of Disulphide Bridges in Par j 2.0101, a Major Allergen of *Parietaria judaica* Pollen" Biol. Chem., 2003, vol. 384, pp. 1165-1172.
Asturias et al., "Par j 1 and Par J 2, the Major Allergens from *Parietaria judaica* Pollen, have Similar Immunoglobulin E Epitopes" Clin. Exp. Allergy, 2003, vol. 33, pp. 518-524.
Ayuso et al., "Isolation by mAb Based Affinity Chromatography of Two Par j I Isoallergens. Comparison of their Physicochemical, Immunochemical and Allergenic Properties" Molecular Immunology, 1993, vol. 30, No. 15, pp. 1347-1354.
Batard et al, "Characterization of Wild-Type Recombinant Bet v 1a as a Candidate Vaccine against Birch Pollen Allergy" Int. Arch. Allergy Immunol, 2005, vol. 136, pp. 239-249.
Beezhold et al., "Lipid Transfer Protein from *Hevea brasiliensis* (Hev b 12), a Cross-Reactive Latex Protein" Ann Allergy Asthma Immunol, 2003, vol. 90, pp. 439-445.
Ceska et al., "A New and Simple Radioimmunoassay Method for the Determination of IgE" Immunochemistry, 1972, vol. 9, pp. 1021-1030.
Colombo et al., "The Allergens of Parietaria" Int. Arch. Allergy Immunol, 2003, vol. 130, pp. 173-179.
Colombo et al., "An Update on Allergens. *Parietaria* Pollen Allergens" Allergy, 1998, vol. 53, pp. 917-921.

(Continued)

*Primary Examiner* — Vanessa L Ford
*Assistant Examiner* — Lakia Tongue
(74) *Attorney, Agent, or Firm* — Lerner, David, Littenberg, Krumholz & Mentlik, LLP

(57) ABSTRACT

The present invention relates to recombinant DNA molecules which encode chimeric polypeptides of differing allergens of *Parietaria judaica* which can be used for the prevention and treatment of allergies, in particular pollen allergies. Specifically, chimeric polypeptides composed of fragments of the allergens Par j 1 and Par j 2 having hypoallergenic characteristics are described. Methods for producing these recombinant polypeptides in heterologous expression systems are also described. Efficient methods of purifying the chimeric proteins are also described.

16 Claims, 15 Drawing Sheets

(56) References Cited

OTHER PUBLICATIONS

Costa et al., "cDNA Cloning, Expression and Primary Structure of Par j I, a major Allergen of *Parietaria judaica* Pollen" FEBS Letters, 1994, vol. 341, pp. 182-186.
Cromwell et al., "Strategies for Recombinant Allergen Vaccines and Fruitful Results from First Clinical Studies" Immunol Allergy Clin N Am, 2006, vol. 26, pp. 261-281.
Díaz-Perales et al., "Lipid-Transfer Proteins as Potential Plant Panallergens: Cross-Reactivity Among Proteins of Artemisia Pollen, Castanea nut and Rosaceae Fruits, with Different IgE-Binding Capacities" Clinical and Experimental Allergy, 2000, vol. 30, pp. 1403-1410.
Duro et al., "cDNA Cloning, Sequence Analysis and Allergological Characterization of Par j 2.0101, a new Major Allergen of the *Parietaria judaica* Pollen" FEBS Letters, 1996, vol. 399, pp. 295-298.
Gonzalez-Rioja et al., "Genetically Engineered Hybrid Proteins from *Parietaria judaica* Pollen for Allergen-Specific Immunotherapy" Journal of Allergy and Clinical Immunology, 2007, vol. 120, No. 3, pp. 602-609.
Hanahan D., "Studies on Transformation of *Escherichia coli* with Plasmids" J. Mol. Biol., 1983, vol. 166, pp. 557-580.
Jutel et al., "Allergen-Specific Immunotherapy with Recombinant Grass Pollen Allergens" Journal of Allergy and Clinical Immunology, 2005, vol. 116, No. 3, pp. 608-613.
Karamloo et al., "Prevention of Allergy by a Recombinant Multi-Allergen Vaccine with Reduced IgE Binding and Preserved T Cell Epitopes" Eur. J. Immunol, 2005, vol. 35, No. 11, pp. 3268-3276.
Laemmli U. K., "Cleavage of Structural Proteins During the Assembly of the Head of Bacteriophage T4" Nature, 1970, vol. 227, pp. 680-685.
Linhart et al., "Molecular Design of Allergy Vaccines" Current Opinion in Immunology, 2005, vol. 17, pp. 1-10.
Miyamoto T., "Increased Prevalence of Pollen Allergy in Japan" in Advance in Allergology and Clinical Immunology, Godard et al., (Cornforth, UK: the Parthenon Publishing Group), 1992, pp. 343-347.
Movérare R., "Immunological Mechanism of Specific Immunotherapy with Pollen Vaccines: Implications for Diagnostics and the Development of improved Vaccination Strategies" Expert Rev. Vaccines, 2003, vol. 2, No. 1, pp. 85-97.
Niederberger et al., "Vaccination with Genetically Engineered Allergens Prevents Progression of Allergic Disease" Proc. National Academy of Science of the USA (PNAS), 2004, vol. 101, Suppl. 2, pp. 14677-14682.
Polo et al., HPLC Purification of the main Allergen of *Parietaria judaica* Pollen Molecular Immunology, 1990, vol. 27, No. 2, pp. 151-157.
Polo et al., "Studies on the Relationship Between Structure and IgE-Binding Ability of *Parietaria judaica* Allergen I" Molecular Immunology, 1991, vol. 28, No. ½, pp. 169-175.
Rodríguez et al., "Allergenic Diversity of the Olive Pollen" Allergy, 2002, vol. 57, Suppl. 71, pp. 6-16.
Tejera et al., "Identification, Isolation, and Characterization of Ole e 7, a new Allergen of Olive Tree Pollen" J. Allergy Clin. Immunol., 1999, pp. 797-802.
Towbin et al., "Electrophoretic Transfer of Proteins form Polyacrylamide gels to Nitrocellulose Sheets: Procedure and Some Applications" Proc. Natl. Acad. Sci. USA, 1979, vol. 76, No. 9, pp. 4350-4354.
Van Ree R., " Clinical Importance of non-Specific Lipid Transfer Proteins as Food Allergens" Biochemical Society Transactions, 2002, vol. 30, Part 6, pp. 910-913.
Von Bubnoff et al., "FcepsilonRI induces the Tryptophan Degradation Pathway Involved in Regulating T Cell Responses" J Immunol, 2002, vol. 169, No. 4, pp. 1810-1816.
Wachholz et al., "Inhibition of Allergen-IgE Binding to B Cells by IgG Antibodies after Grass Pollen Immunotherapy" J Allergy Clin Immunol, 2003, vol. 112, No. 5, pp. 915-922.
Colombo et al. (1998) "Identification of an Immunodominant IgE Epitope of the *Parietaria judaica* Major Allergen" Journal of Immunology 160(6) 2780-2785.
Gonzalez-Rioja et al. (2007) "Genetically Engineered Hybrid Proteins from *Parietaria judaica* Pollen for Allergen-Specific Immunotherapy" Journal of Allergy and clinical Immunology 120(3) 602-609.
Colombo, et al., 1998. "Identification of an Immunodominant IgE epitope of the *Parietaria judaica* Major Allergen". Journal of Immunology 160(6): 2780-2785.
Asturias, et al., 2003. "Par j 1 and Par j 2, the Major Allergens From *Parietaria judaica* Pollen, Have Similar Immunoglobulin E Epitopes". Clinical and Experimental Allergy 33(4): 518-524.
Linhart, et al., 2005. "Molecular Design of Allergy Vaccines". Current Opinion in Immunology 17(6): 646-655.
Ferreira, et al., 2002. "Genetic Engineering of Allergens: Future Therapeutic Products". International Archives of Allergy and Immunology 128(3): 171-178.
Bannon, et al., 2006. "Evaluation of Available IgE-binding Epitope Data and its Utility in Bioinformatics". Molecular Nutrition & Food Research 50(7): 638-644.
Carreira, J. and Polo, F. (1995), "The allergens of *Olea europaea* and *Parietaria* spp. and their relevance in the Mediterranean Area," Allergy Clin. Immunol. News 7, 79-84, Hogrefe & Huber Publishers (1995).
International Search Report (PCT/ISA/210) for PCT/IB2009/005114 issued on Oct. 16, 2009.
P.L. Bhalla et al.,-"Biotechnology-based allergy diagnoses and vaccination," Trends in Biotechnology, Jan. 28, 2008, pp. 153-161, vol. 26, No. 3, Elsevier Publications, Cambridge, GB, XP022487059.
M Wallner et al., "Allergy multivaccines created by DNA shuffling of tree pollen allergens," Journal of Allergy and Clinical Immunology, Jul. 29, 2007, pp. 374-380, vol. 120, No. 2, Mosby-Yearly Book, Inc., US, XP022199094.
K.W. Chen et al., "Reduction of the in vivo allergenicity of Der p. 2, the major house-dust mite allergen, by genetic engineering," Molecular Immunology, Mar. 4, 2008, pp. 2486-2498, vol. 45, No. 9, Pergamon, GB, XP022540428.
R. Gonzalez-Rioja et al., "Genetically engineered hybrid proteins from *Parietaria judaica* pollen for allergen-specific immunotherapy," Journal of Allergy and Clinical Immunology, Aug. 31, 2007, pp. 602-609, Mosby-Yearly Book, Inc., US, XP022212638.
R. Crameri et al., Novel vaccines and adjuvants for allergen-specific immunotherapy, Current Opinion in Immunology, Dec. 1, 2006, pp. 761-768, Elsevier, Oxford, GB, XP025078999.
J. Holm et al., "Allergy vaccine engineering: Epitope modulation of recombinant Bet v 1 reduces IgE binding but retains protein folding pattern for induction of protective blocking-antibody responses," Journal of Immunology, Oct. 25, 2004, pp. 5258-5267, vol. 173, No. 8, XP009123652.
R. Mantyjarvi et al., "Lipocalins as allergens," Biochimica et Biophysica Acta—Protein Structure and Molecular Enzymologie, Oct. 18, 2000, pp. 308-317, vol. 1482, No. 1-2, Elsevier Science BV, Amsterdam, NL, XP004279083.
M. Akdis et al., "Mechanisms of allergen-specific immunotherapy," Journal of Allergy and Clinical Immunology, Apr. 5, 2007, pp. 780-789, vol. 119, No. 4, Mosby-Yearly Book, Inc., US, XP022020511.
G. Bannon et al., "Evaluation of available IgE-binding epitope data and its utility in bioinformatics," Molecular Nutrition & Food Research, Jul. 1, 2006, vol. 50, No. 7, Wiley-VCH Verlag, Weinheim, DE, XP002448731.

* cited by examiner

```
ATGAGAGGATCTCACCATCACCATCACCATGGGATCCTGCAAGAAACCTGC
 M  R  G  S  H  H  H  H  H  H  G  I  L  Q  E  T  C

GGGACTATGGTGAGAGCGCTGATGCCGTGCCTGCCGTTCGTGCAGGGGAAA
 G  T  M  V  R  A  L  M  P  C  L  P  F  V  Q  G  K

GAGAAAGAGCCGTCAAAGGGGTGCTGCAGCGGCGCCAAAAGATTGGACGGG
 E  K  E  P  S  K  G  C  C  S  G  A  K  R  L  D  G

GAGACGAAGACGGGGCCGCAGAGGGTGCACGCTTGTGAGTGCATCCAGACC
 E  T  K  T  G  P  Q  R  V  H  A  C  E  C  I  Q  T

GCCATGAAGACTTATTCCGACATCGACGGGAAACTCGTCAGCGAGGTCCCC
 A  M  K  T  Y  S  D  I  D  G  K  L  V  S  E  V  P

AAGCACTGCGGCATCGTTGACAGCAAGCTCCCGCCCATTGACGTCAACATG
 K  H  C  G  I  V  D  S  K  L  P  P  I  D  V  N  M

GACTGCAAGACACTTGGAGTGGTTCCTCGGCAACCCCAACTTCCAGTCTCT
 D  C  K  T  L  G  V  V  P  R  Q  P  Q  L  P  V  S

CTCCGTCATGGTCCCGTCACGGGCCCAAGTGATCCGCCCACAAAGCACGG
 L  R  H  G  P  V  T  G  P  S  D  P  A  H  K  A  R

TTGGAGAGACCCCAGATTAGAGTTCCGCCCCCCGCACCGGAAAAAGCCGAA
 L  E  R  P  Q  I  R  V  P  P  P  A  P  E  K  A  E

TTCGAGGAGGCTTGCGGGAAAGTGGTGCAGGATATAATGCCGTGCCTGCAT
 F  E  E  A  C  G  K  V  V  Q  D  I  M  P  C  L  H

TTCGTGAAGGGGGAGGAGAAGGAGCCGTCGAAGGAGTGCTGCAGCGGCACG
 F  V  K  G  E  E  K  E  P  S  K  E  C  C  S  G  T

AAGAAGCTGAGCGAGGAGGTGAAGACGACGGAGCAGAAGAGGGAGGCCTGC
 K  K  L  S  E  E  V  K  T  T  E  Q  K  R  E  A  C

AAGTGCATAGTGCGCGCCACGAAGGGCATCTCCGGTATCAAAAATGAACTT
 K  C  I  V  R  A  T  K  G  I  S  G  I  K  N  E  L

GTCGCCGAGGTCCCCAAGAAGTGCGATATTAAGACCACTCTCCCGCCCATC
 V  A  E  V  P  K  K  C  D  I  K  T  T  L  P  P  I

ACCGCCGACTTCGACTGCTCCAAGATCCAAAGTACTATTTTCAGAGGTTAC
 T  A  D  F  D  C  S  K  I  Q  S  T  I  F  R  G  Y

TAT
 Y
```

FIGURE 2

```
ATGAGAGGATCTCACCATCACCATCACCATGGGATCCTGCAAGAAACCTGC
 M   R   G   S   H   H   H   H   H   H   G   I   L   Q   E   T   C

GGGACTATGGTGAGAGCGCTGATGCCGTGCCTGCCGTTCGTGCAGGGGAAA
 G   T   M   V   R   A   L   M   P   C   L   P   F   V   Q   G   K

GAGAAAGAGCCGTCAAAGGGGCTGCAGATCCAGACCGCCATGAAGACTTAT
 E   K   E   P   S   K   G   L   Q   I   Q   T   A   M   K   T   Y

TCCGACATCGACGGGAAACTCGTCAGCGAGGTCCCCAAGCACTGCGGCATC
 S   D   I   D   G   K   L   V   S   E   V   P   K   H   C   G   I

GTTGACAGCAAGCTCCCGCCCATTGACGTCAACATGGACTGCAAGACACTT
 V   D   S   K   L   P   P   I   D   V   N   M   D   C   K   T   L

GGAGTGGTTCCTCGGCAACCCCAACTTCCAGTCTCTCTCCGTCATGGTCCC
 G   V   V   P   R   Q   P   Q   L   P   V   S   L   R   H   G   P

GTCACGGGCCCAAGTGATCCCGCCCACAAAGCACGGTTGGAGAGACCCCAG
 V   T   G   P   S   D   P   A   H   K   A   R   L   E   R   P   Q

ATTAGAGTTCCGCCCCCCGCACCGGAAAAAGCCGAATTCGAGGAGGCTTGC
 I   R   V   P   P   P   A   P   E   K   A   E   F   E   E   A   C

GGGAAAGTGGTGCAGGATATAATGCCGTGCCTGCATTTCGTGAAGGGGGAG
 G   K   V   V   Q   D   I   M   P   C   L   H   F   V   K   G   E

GAGAAGGAGCCGTCGAAGGAGGATATCATAGTGCGCGCCACGAAGGGCATC
 E   K   E   P   S   K   E   D   I   I   V   R   A   T   K   G   I

TCCGGTATCAAAAATGAACTTGTCGCCGAGGTCCCCAAGAAGTGCGATATT
 S   G   I   K   N   E   L   V   A   E   V   P   K   K   C   D   I

AAGACCACTCTCCCGCCCATCACCGCCGACTTCGACTGCTCCAAGATCCAA
 K   T   T   L   P   P   I   T   A   D   F   D   C   S   K   I   Q

AGTACTATTTTCAGAGGTTACTAT
 S   T   I   F   R   G   Y   Y
```

FIGURE 5

```
ATGAGAGGATCTCACCATCACCATCACCATGGGATCCTGCCAGAAACCTGC
 M  R  G  S  H  H  H  H  H  G  I  L  P  E  T  C

GGGACTATGGTGAGAGCGCTGATGCCGTGCCTGCCGTTCGTGCAGGGGAAA
 G  T  M  V  R  A  L  M  P  C  L  P  F  V  Q  G  K

GAGAAAGAGCCGTCAAAGGGGCTGCAGATCCAGACCGCCATGAAGACTTAT
 E  K  E  P  S  K  G  L  Q  I  Q  T  A  M  K  T  Y

TCCGACATCGACGGGAAACTCGTCAGCGAGGTCAGATCTAGCAAGCTCCCG
 S  D  I  D  G  K  L  V  S  E  V  R  S  S  K  L  P

CCCATTGACGTCAACATGGACTGCAAGACACTTGGAGTGGTTCCTCGGCAA
 P  I  D  V  N  M  D  C  K  T  L  G  V  V  P  R  Q

CCCCAACTTCCAGTCTCTCTCCGTCATGGTCCCGTCACGGGCCCAAGTGAT
 P  Q  L  P  V  S  L  R  H  G  P  V  T  G  P  S  D

CCCGCCCACAAAGCACGGTTGGAGAGACCCCAGATTAGAGTTCCGCCCCCC
 P  A  H  K  A  R  L  E  R  P  Q  I  R  V  P  P  P

GCACCGGAAAAAGCCGAATTCGAGGAGGCTTGCGGGAAAGTGGTGCAGGAT
 A  P  E  K  A  E  F  E  E  A  C  G  K  V  V  Q  D

ATAATGCCGTGCCTGCATTTCGTGAAGGGGGAGGAGAAGGAGCCGTCGAAG
 I  M  P  C  L  H  F  V  K  G  E  E  K  E  P  S  K

GAGGATATCATAGTGCGCGCCACGAAGGGCATCTCCGGTATCAAAAATGAA
 E  D  I  I  V  R  A  T  K  G  I  S  G  I  K  N  E

CTTGTCGCCGAGGTCCCCGGTACCCTCCCGCCCATCACCGCCGACTTCGAC
 L  V  A  E  V  P  G  T  L  P  P  I  T  A  D  F  D

TGCTCCAAGATCCAAAGTACTATTTTCAGAGGTTACTAT
 C  S  K  I  Q  S  T  I  F  R  G  Y  Y
```

FIGURE 8

HYPOALLERGENIC CHIMERIC PROTEINS BELONGING TO THE LIPID TRANSFER FAMILY OF *PARIETARIA JUDAICA* FOR USE IN THE TREATMENT OF ALLERGIES

CROSS REFERENCE TO RELATED APPLICATIONS

The present application is a U.S. national phase of PCT/IB2007/001025 filed Apr. 11, 2007, which claims the benefit of Spanish Patent Application No. 200600955, filed on Apr. 12, 2006, both of which are incorporated by reference herein.

The present invention relates to the field of the production of chimeric proteins for the prevention and treatment of allergies, in particular pollen allergies and most particularly allergies caused by allergens from the lipid transfer protein family and more specifically those found in pollen from species of *Parietaria*.

BACKGROUND OF THE INVENTION

Type I allergies are a significant health problem in industrialised countries. This type of allergy is caused by the formation of IgE antibodies against antigens carried by the air. These IgE antibodies interact with the mast cells and basophiles, liberating biological mediators such as histamine, and causing allergic rhinitis, conjunctivitis and bronchial asthma in about 20% of the population [(1) Miyamoto, T. (1992). Increased prevalence of pollen allergy in Japan. In Advances in Allergology and Clinical Immunology. P. Godard, J. Bousquet, and F. B. Michel, eds. (Cornforth, U K: The Parthenon Publishing Group), pp. 343-347].

Specific immunotherapy (SIT) is an effective treatment for allergic reactions triggered by specific allergens and basically consists in modulating the immune response in the patient by the regular administration, in increasing concentrations, of the proteins which produce the allergy (allergenic extracts). High doses of the injected allergens induce the high synthesis of IL-12 by the antigen-presenting cells, for example the dendritic cells, which preferably promote the development of T cells which are cooperative virgin cells ($nT_H$) toward $T_H1$ or $T_H0$. This allows a deviation from the immune response of the allergic response type related to the $T_H2$ cells toward a $T_H1/T_H0$ type response which leads to the production of high levels of IFN-γ [(2) Akdis, C. A. and Blaser, K. (2000). Mechanisms of allergen-specific immunotherapy. Allergy 55, 522-530]. The immune deviation is reinforced by the induction of the tolerance (an energy or clonal deletion) of $T_H2$ memory cells under the influence of regulating T cells ($T_R1$) which produce the immunosuppressor cytokines IL-10 and TGF-β [(3) Akdis, C. A., Joss, A., Akdis, M., and Blaser, K. (2001). Mechanism of IL-10 induced cell inactivation in allergic inflammation and normal response to allergens. Int. Arch Allergy Immunol. 124; 180-182]. The reduction in the activation and proliferation of the $T_H2$ cells is accompanied by reduced production of IL-4, and of IgEs by the B cells. The reduction in the activity and infiltration of the $T_H2$ cells into the nasal and bronchial mucus results in reduced IL-5 synthesis, allowing a reduction in eosinophile infiltration which leads to a great reduction in the liberation of inflammatory mediators such as MBP and ECP proteins. The new specific clones of T cells of predominant phenotype allergen $T_H0$ produce a mixture of $T_H1$ and $T_H2$ type cytokines promoting the production of a large quantity of specific IgG allergen antibodies by the B cells. On the other hand, the high levels of IL-10 induce the high synthesis of specific IgG4 allergen antibodies. These two types of specific antibodies can act as blocking antibodies providing the intersection of the IgE antibodies combined with their receptors in the mast cells and therefore inhibiting the degranulation and liberation of histamine [(4) Moverate, R. (2003). Immunological mechanisms of specific immunotherapy with pollen vaccines: implications for diagnostics and the development of improved vaccination strategies. Expert Rev. Vacc. 2, 85-97; (5) Wachholz, P. A., Soni, N. K., Till, S., and Durham, S. R. (2003). Inhibition of allergen-IgE binding to B cells by IgG antibodies after grass pollen immunotherapy. J. Allergy Clin. Immunol. 112; 915-922]. They also block the collection of IgE-mediated antigen by the antigen-containing cells, and this suppresses the immune reaction to the allergens.

The allergen extracts isolated from natural sources are complex mixtures of proteins and other molecules. Their composition, and therefore allergenicity, depends on the material used, which varies according to the ambient conditions, the state of maturation in the case of pollens and the conditions of growth of mites, etc., in the case of fungi, etc. Some extracts can even contain an inadequate concentration of major allergens and can even be contaminated with undesirable components to which the patient is not allergic, or both. Current immunotherapy uses complete allergen extracts exclusively, and this leads to a number of problems such as:

serious adverse reactions owing to the reactivity of the vaccine with IgE of the effector cells[[.]];

appearance of new sensitisation to other allergens present in the vaccine after immunotherapy[[.]]; and difficulties in standardisation of the allergen extracts.

All this means that immunotherapy is not a treatment which is as safe and effective as desired. Better knowledge of the pathogenesis of allergy and of the mechanisms of the specific immunotherapy has made it possible to get closer to the solution to the aforementioned problems. Knowledge of the influence of the IgE-mediated antigen in the specific allergen response $T_H2$ has increased efforts to create allergens which do not bind IgE. The main object of current specific immunotherapy is to modify the allergen with the aim of inactivating the IgE epitopes, thus reducing and even eliminating the bond to IgE and consequently the adverse reactions [(6) Valenta, R. and Linhart, B. (2005). Molecular design of allergy vaccines. Curr. Opin. Immunol. 17, 1-10]. In this way, the modified allergen will be directed toward the T cells by a phagocytosis/pinocytosis-mediated antigen collection mechanism, preventing the IgE intersection and the presentation of IgE-dependent antigen. This induces a balance in $T_H0$ or $T_H1$ cytokine production by the T cells, less production of IgE and more production of IgG by the B cells; all this will lead to the induction of $T_H2$ type T cell tolerance without a risk of anaphylaxis. Progress in recombinant methods of obtaining allergens and allergen derivatives has allowed a great increase in the capacity for developing new vaccines for the treatment of allergies. This has been possible owing to the possibility of mutating or deleting significant amino acids of IgE epitopes, as well as the fractionation and oligomerisation thereof for obtaining hypoallergenic vaccines. These molecules which have a lesser capacity to bind IgE but maintain their reactivity toward T cells may be administered in greater doses, allowing faster and safer immunotherapy with a smaller number of injections. In addition, recombinant allergens may be produced on a large scale in fermentation tanks, using microbial expression systems, and the purification thereof is more efficient and inexpensive than that of their natural equivalents. The use of hypoallergenic derivatives in immunotherapy has previously been described using fragments of trimers of Bet v 1 [(7) Niederberger, V., Horak, F., Vrtala, S., Spitzauer, S., Krauth, M. T., Valent, P., Reisinger, J., Pelzmann, M., Hayek, B., Kronqvist, M., Gafvelin, G., Grönlund, H., Purohit, A., Suck, R., Fiebig, H., Cromwell, O., Pauli, G., van Hage-Hamsten, M., and Valenta, R. (2004). Vaccination with genetically engineered allergens prevents progression of allergic disease. Proc. Natl. Acad. Sci. U.S.A. 101, 14677-14682], multi-allergenic hybrids of bee venon proteins (Api m 1, 2, 3) [(8) Schmid-Grendelmeier, P., Karamloo, F., Müller, U., Housley-Marcovic, Z., Soldatova, L., Zumkehr, J., Kemeny, D. M., Kündig, T., Reimers, A., von Beust, B. R., Salagianni, M., Akdis, M., Kussebi, F., Spangfort, M. D., Blaser, K., and Akdis, C. A. (2005). Prevention of allergy by a recombinant multi-allergen vaccine with reduced IgE binding and preserved T cell epitopes. Eur. J. Immunol. 35, 3268-3276] and mutated fusions of Par j 2 and Par j 1 for eliminating their tertiary structure.

Some authors mention that allergenic vaccines should not be made with hypoallergens since the bond to IgE could facilitate the capture and presentation of the allergen by the professional antigen-presenting cells, as dendritic cells and activated B lymphocyte cells, which express surface receptors for IgE of both high affinity and low affinity. This approach has a special meaning when using the sublingual route in immunotherapy. The intersection of high affinity receptors can also lead to a reduction in the response of the T cells toward the allergens [(9) Allam, J. P., Novak, N., Fuchs, C., Asen, S., Berge, S., Appel, T., et al. (2003) Characterization of dendritic cells from human oral mucosa: a new Langerhans' cell type with high constitutive FcεRI expression. J. Allergy Clin. Immunol. 112, 141-8. (10) von Bubnoff, D., Matz, H., Frahnert, C., Rao, M. L., Hanau, D., de la Salle, H., Bieber, T. (2003) FcεRI induces the triptophan degradation pathway involved in regulating T cell responses. J. Immunol. 169, 1810-1816]. Many researchers are still making this type of vaccine without introducing deletions [(11) Batard, T., Didierlaurent, A., Chabre, H., Mothes, N., Bussieres, L., Bohle, B., et al. (2005) Characterization of wild-type recombinant Bet v 1a as a candidate vaccine against birch pollen allergy. Int. Arch. Allergy Immunol. 136, 239-249. (12) Jutel, M., Jaeger, L., Suck, R., Meyer, H., Fiebig, H., Cromwell, O. (2005) Allergen-specific immunotherapy with recombinant grass pollen allergens. J. Allergy Clin. Immunol. 116, 608-13. (13) Niederberger, V., Horak, F., Vrtala, S., Spitzauer, S., Krauth, M. T., Valent, P., et al. (2004) Vaccination with genetically engineered allergens prevents progression of allergic disease. Proc. Natl. Acad. Sci. U.S.A. 101, 14677-82. (14) Cromwell, O., Fiebig, H., Suck, R., Kahlert, H., Nandy, A., Kettner, J., et al. (2006) Strategies for recombinant allergen vaccines and fruitful results from first clinical studies. Immunol. Allergy Clin. N. Am. 26, 261-81].

Parietaria is a genus of dicotyledon weed from the Urticaceae family, and the Urticales order. Various species of the Parietaria genus are widely and abundantly distributed along the Mediterranean coast [(15) Colombo, P., Duro, G., Costa, M. A., Izzo, V., Mirisola, M., Locorotondo, G., Cocchiara, R., and Geraci, D. (1998). An update on allergens. Parietaria pollen allergens. Allergy 53, 917-921]. The most common species are P. judaica and P. officinalis, but other species such as P. lusitanica, P. mauritanica, and P. cretica, may have some presence in some regions. Nevertheless, the Mediterranean regions are not the only ones where Parietaria pollen can be found, since its presence has been described in the South of England, Austria, temperate regions of central and eastern Europe Australia and California [(16) Colombo, P., Bonura, A., Costa, M., Izzo, V., Passantino, R., Licorotondo, G., Amoroso, S., and Gerasi, D. (2003). The allergens of Parietaria. Int. Arch. Allergy Immunol. 130, 173-179; (17) Carreira, J. and Polo, F. (1995). The allergens of Olea europaea and Parietaria spp. and their relevance in the Mediterranean Area. Allergy Clin. Immunol. News 7, 79-84]. A significant characteristic of Parietaria is the long pollenisation period which lasts for a plurality of months and results in the presence of almost perennial symptoms in patients who are allergic to Parietaria, ranging from slight rhinoconjunctivitis to severe asthma. It should be noted that the normal light monospecific sensitisation to Parietaria involves the sensitisation to various species of this genus, since significant crosswise reactivity has been demonstrated between differing species of Parietaria.

Various papers have been presented on the purification and characterisation of allergenic fractions of the two most common species which are P. judaica and P. officinalis. These fractions have molecular weights in the range from 10-14 kDa and are responsible for virtually the entire allergenic power of their extracts [(16) Colombo, P., Bonura, A., Costa, M., Izzo, V., Passantino, R., Licorotondo, G., Amoroso, S., and Gerasi, D. (2003). The allergens of Parietaria. Int. Arch. Allergy Immunol. 130, 173-179; (18) Ayuso, R., Carreira, J., Lombardero, M., Duffort, O., Peris, A., Basomba, A., and Polo, F. (1993). Isolation by mAb based affinity chromatography of two Par j isoallergens. Comparison of their physicochemical, immunochemical and allergenic properties. Mol. Immunol. 30, 1347-1354; (19) Polo, F., Ayuso, R., and Carreira, J. (1990). HPLC purification of the main allergen of Parietaria judaica pollen. Mol. Immunol. 27, 151-157; (20) Polo, F., Ayuso, R., and Carreira, J. (1991). Studies on the relationship between structure and IgE-binding ability of Parietaria judaica allergen I. Mol. Immunol. 28, 169-175]. The development of recombinant DNA technology has enabled the molecular characterisation of Parietaria pollen allergens to be completed: the two major allergens of P. judaica pollen known as Par j 1 and Par j 2 have been cloned and sequenced [(21) Duro, G., Colombo, P., Costa, M. A., Izzo, V., Porcasi, R., DiFiore, R., Locorotondo, G., Mirisola, M. G., Cocchiara, R., and Geraci, D. (1996). cDNA cloning, sequence analysis and allergological characterization of Par j 2.0101, a new major allergen of the Parietaria judaica pollen. FEBS Lett. 399, 295-298; (22) Costa, M. A., Colombo, P., Izzo, V., Kennedy, H., Venturella, S., Cocchiara, R., Mistrello, G., Falagiani, P., and Geraci, D. (1994). cDNA cloning expression and primary structure of Par j 1, a major allergen of Parietaria judaica pollen. FEBS Lett. 341, 182-186; (23) Amoresano, A., Pucci, P., Duro, G., Colombo, P., Costa, M. A., Izzo, V., Lambda, D., and Geraci, D. (2003). Assignment of disulphide bridges in Par j 2.0101, a major allergen of Parietaria judaica pollen. Biol. Chem. 384, 1165-1172]. Both allergens belong to the family of non-specific lipid transfer proteins (ns-LTP) and possess a signal peptide in their terminal region which, after processing, gives rise to proteins having a molecular weight of 14,726 and 11,344 Da respectively and having about 45% of identical residues. The possible IgE-binding linear epitopes in both allergens, which would be situated in structurally related zones, have been described [(24) Asturias, J. A., Gómez-Bayón, N., Eseverri, J. L., and Martinez, A. (2003). Par j 1 and Par j 2, the major allergens from Parietaria judaica pollen, have similar immunoglobulin E epitopes. Clinical and Experimental Allergy 33, 518-524]. These regions are the targets which will be acted upon in order to be able to obtain the optimum hypoallergenic molecules for the treatment of the allergy to P. judaica pollen.

The ns-LTP are well known for their capacity to complete in vitro the intermembrane interchange and/or the transfer of polar lipids [(25) van Ree, R. (2002). Clinical importance of non-specific lipid transfer proteins as food allergens. Biochem. Soc. Trans 30, 910-913]. Two main families have been characterised in plants, LTP1 with a molecular mass of approximately 9 kDa and LTP2 with a molecular mass of approximately 7 kDa. Allergens belonging to the LTP family have been identified in plants other than foods, where they have been widely studied. Thus, Hev b 12 from the latex of *Hevea brasiliensis* is a basic 9.3 kDa protein which demonstrates about 65% sequence identity with allergenic LTPs of fruits of the Rosaceae family [(26) Beezhold, D. H., Hickey, V. L., Kostyal, D. A., and et al. (2003). Lipid transfer protein from *Hevea brasiliensis* (Hev b 12), a cross-reactive latex protein. Ann Allergy Asthma Immunol 439-445]. In addition, some pollen allergens have been described as LTPs, such as Art v 3 of *Artemisia vulgaris* [(27) Diaz-Perales, A., Lombardero, M., Sanchez-Monge, R., and et al. (2000). Lipid-transfer proteins as potential plant panallergens: cross-reactivity among proteins of *Artemisia* pollen, Castanea nut and Rosaceae fruits, with different IgE-binding capacities. Clin Exp Allergy 1403-1410] and Ole e 7 of *Olea europaea* [(28) Tejera, M. L., Villalba, M., Batanero, E., and Rodriguez, R. (1999). Identification, isolation, and characterization of Ole e 7, a new allergen of olive tree pollen. J. Allergy Clin. Immunol. 797-802; (29) Rodriguez, R., Villalba, M., Batanero, E., and et al. (2002). Allergenic diversity of the olive pollen. Allergy 6-16] which are of 9-10 kDa and have 30-55% sequence identity with allergenic LTPs of foods. The major allergens of *P. judaica*, Par j 1 and Par j 2, which have about 45% sequence identity with one another, on the other hand, have higher molecular weights than normal in the LTPs family; 14.7 and 11.3 kDa, respectively [(16) Colombo, P., Bonura, A., Costa, M., Izzo, V., Passantino, R., Licorotondo, G., Amoroso, S., and Gerasi, D. (2003). The allergens of *Parietaria*. Int. Arch. Allergy Immunol. 130, 173-179]. However, although both allergens have a similar structure to that of the LTPs, they have moderate levels of identity with food LTPs in the common sequence region (28% between Par j 1 and peach LTP).

WO2005/085278 discloses the construction of a fusion protein comprising the two major allergens of *Parietaria judaica*, wherein the three-dimensional structure of the fusion protein has been disrupted by replacement of certain cysteine residues in the primary sequence of each allergen (more specifically the cysteine residues involved in the formation of disulphide bridges) so that the sequences of allergens maintain essentially the same length. According to later experiments, this should lead to a protein that is 1000 times less allergenic than natural allergens.

The inventors of the present invention have discovered that a surprisingly large reduction in allergenicity can be obtained not only by disrupting the three-dimensional structure of the allergen but also by deletion of some IgE-binding sites (known as B epitopes) and that, most surprisingly, this does not lead to a reduction in immunogenicity.

The present invention discloses for the first time differing chimeric proteins obtained by binding fragments of the two allergens of *Parietaria judaica* (Par j 1 and Par j 2) containing a smaller number of IgE-binding epitopes, as well as differing methods and intermediates for obtaining them. Not only is the three-dimensional structure of the chimeric proteins of the present invention disrupted but also certain B epitopes have been deleted. The chimeric proteins according to the present invention can be called hypoallergenic with an allergenicity reduced by 99.99%, as they have a lower capacity to bind IgE antibodies based on: i) in vitro ELISA, ELISA inhibition and immunodetection tests using mixtures of sera from patients allergic to *P. judaica*; ii) in vivo tests of cutaneous reactivity in patients allergic to *P. judaica*; and iii) in vitro EAST inhibition test with individualised sera from patients allergic to *P. judaica*. The chimeric proteins according to the present invention, on the other hand, maintain their immunogenic capacity, as demonstrated by lymphoproliferation tests on peripheral blood mononuclear cells (CMSP) from 13 patients allergic to *P. judaica*.

The allergenic extracts are complex mixtures of proteins and non-protein molecules. The increasing use of techniques for detecting the levels of specific IgE against the components of an extract has made it possible to demonstrate that allergic patients usually have reactivity toward various components. Cases of allergic patients who react only to a single allergen are rare. Since allergenic extracts have obvious problems in immunotherapy, one solution is to group as many therapeutic properties as possible in a single molecule.

SUMMARY OF THE INVENTION

The present inventors have succeeded in combining two allergens in one molecule, this having not only benefits from the point of view of industrial production and therapy, but also showing significantly reduced allergenicity with no change in immunogenicity.

For these reasons, the present invention relates to chimeric proteins (hereinafter called Q1, Q2, and Q3) composed of fragments of the allergens Par j 1 and Par j 2, of which the allergenic reactivity is reduced without a loss of immunogenic capacity, as they have lost some of their IgE-binding B epitopes. In this way, the resultant chimeric polypeptide has a lower molecular weight than the sum of the two individual proteins.

The present invention also relates to the nucleotide sequence which includes the DNA that encodes the aforesaid chimeric polypeptide, the expression system comprising said sequence accompanied by the sequences required for expression and control, and the receptor cell transformed by said expression system.

This invention also relates to the clinical use of this chimeric polypeptide, to the specific immunotherapy for the treatment of allergies, as well as to possible compositions in which this chimeric polypeptide occurs and the different methods of administration thereof.

The hypoallergenic properties of the chimeric proteins of the present invention which allow the use thereof in immunotherapy have been widely demonstrated. Immunological tests carried out by the inventors show that the chimera Q2 has no recognition of IgE in sera of patients allergic to *Parietaria judaica*, as illustrated in FIGS. 10 and 11. Q2 has an IgE-binding capacity which is 10,000 times less than that of the mixture of the two natural proteins, as illustrated in FIG. 12.

This low allergenicity data was restrained by in vivo experiments in 30 patients by a skin prick test. The allergenicity of the chimera Q1 was 3.5 times less than that obtained with the two isolated natural proteins (FIG. 13). On the other hand, the allergenicity of Q2, formed by fragments of Par j 1 and Par j 2, which did not contain any of the described B epitopes, was 112 times less than that obtained with the two isolated natural proteins.

The low allergenicity (IgE-binding capacity) of the chimera Q2 was corroborated by measuring the reactivity of this molecule with sera of 30 patients allergic to *Parietaria judaica* (FIG. 14). This reduction in the allergenicity was surprisingly accompanied by maintenance of the immunogenic capacity of the chimera Q2, which did not differ from that of the sum of the individual natural proteins (FIG. 16).

Maintenance of the immunogenicity will enable this chimera to be used as a substitute for the complete extract but much more safely (less allergenicity).

Deposit of Strains

The strain of the microorganism corresponding to the present invention was deposited in the Spanish collection of type cultures (CECT) at the University of Valencia (Universidad de Valencia, Edificio de Investigación, Campus de Burjasot, 46100 BURJASOT, Valencia) in accordance with the Budapest treaty on the international recognition of the deposit of microorganisms for the purposes of patent procedures, with the following reference:

X *Escherichia coli* CECT 7141

Deposited on 7 Mar. 2006.

DESCRIPTION OF DRAWINGS

FIG. 2 shows a sequence of amino acids (SEQ ID NO:2) and nucleotides (SEQ ID NO:1) of Q1. The residues corresponding to the affinity tail of the vector pQE-32 are underlined. The residues introduced by the EcoRI (EF) section are shaded. The cysteine residues have double underlining a FIG. 3 shows a comparison of the IgE epitopes of Par j 1 and Par j 2 (boxes) and the T epitope (underlined), indicating the Q2 deleted epitopes in thick-lined boxes. The identical residues (:) and similar residues (.) have been labeled.

FIG. 5 shows a sequence of amino acids (SEQ ID NO:4) and nucleotides (SEQ ID NO:3) of Q2. The residues corresponding to the affinity tail of the vector pQE-32 are underlined. The residues introduced by the EcoRI (EF) PstI (LQ), and Ecor RV (DI) section are shaded. The cysteine residues have double underlining.

FIG. 8 shows a sequence of amino acids (SEQ ID NO:6) and nucleotides (SEQ ID NO:5) of Q3. The residues corresponding to the affinity tail of the vector pQE-32 are underlined. The residues introduced by the EcoRI (EF) PstI (LQ), and Ecor RV (DI), BglII (RS), and KpnI (GT) section are shaded. The cysteine residues have double underlining.

DETAILED DESCRIPTION

Figure 1:
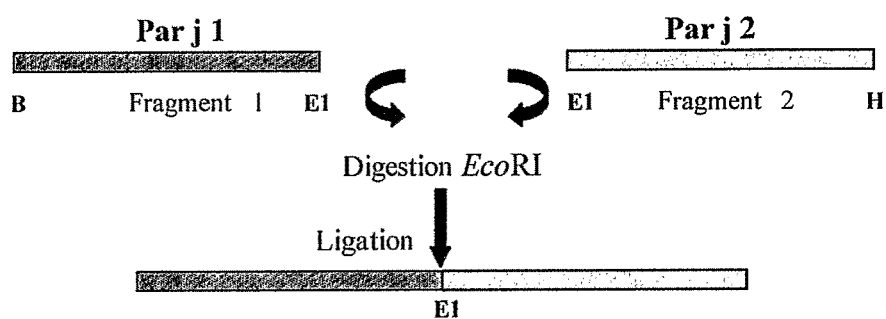
FIG. 1 is a constructional diagram of Q1.

According to one aspect of the present invention, there is provided a chimeric protein or peptide of low allergenicity obtained by deletion of any B epitope or IgE-binding epitode or synthesis without any B epitope or IgE-binding. Deletion will preferably apply to the B epitopes in positions 28 to 53 of Par j 1 and Par j 2.

The term "low allergenicity", and similar variants as used herein is a relative term and relates to the reduced in vivo and in vitro ability of the proteins and peptides of the invention to stimulate an allergic response when compared with the same ability of wildtype immunogens.

Preferably the chimeric protein comprises the amino acid sequence shown in SEQ ID No.: 2, 4 or 6, most preferably the chimeric protein comprises the amino acid sequence shown in SEQ ID No.: 4.

The chimeric protein may alternatively or additionally comprise a sequence homologous to the amino acid sequence shown in SEQ ID No.: 2, 4 or 6. Preferably the homologous sequence has a homology of at least 70%, more preferably at least 80%, more preferably still at least 90%, most preferably 100%, to the amino acid sequence shown in SEQ ID No.: 2, 4 or 6, most preferably to the acid sequence shown in SEQ ID No.: 4.

Another preferred embodiment includes a chimeric protein or peptide having an amino acid sequence with at least 70%, preferably at least 80%, more preferably at least 90%, most preferably 100%, homology to the amino acid sequence shown in SEQ ID No.: 2, 4 or 6.

The chimeric protein may also comprise a peptide sequence facilitating its purification. Such peptides are commonly known in the art, for example a polyhistidine tail.

The fragments constituting the chimeric proteins can be synthesised by a qualified trained person following a known scheme by amplification in the polymerase chain (PCR). Said fragments, after being digested by appropriate restriction enzymes, can integrate by ligation to an expression vector. This expression vector (like the commercial vector pQE32) may have the ability to fuse the chimeric protein with sequences which assist purification such as a series of histidines positioned at the terminal amino end. During the construction of the chimeric proteins, the differing DNA fragments are bound by linkers formed by recognised sequences by differing restriction enzymes, and residues which did not exist in the original sequence of the natural allergen therefore appear in the final chimeric molecule. These new residues, which did not interfere in the correct reading of the protein, have been marked in the sequences in FIGS. 2, 5, and 8, and are appropriately described in the relevant examples. Similarly, the chimeras have 14 residues in the amino-terminal zone which are not present in the original sequence and would correspond to the histidine-rich region which allows rapid purification by interaction with divalent metals bound to solid supports.

According to a second aspect of the present invention, there is provided a polynucleotide encoding a protein or peptide of the invention.

Preferably the polynucleotide comprises the nucleotide sequence shown in SEQ ID No.: 1, 3 or 5, most preferably the polynucleotide comprises the nucleotide sequence shown in SEQ ID No.: 3.

The polynucleotide may alternatively or additionally comprise a sequence homologous to the nucleotide sequence shown in SEQ ID No.: 1, 3 or 5. Preferably the homologous sequence has a homology of at least 70%, more preferably at least 80%, more preferably still at least 90%, most preferably at least 95%, to the nucleotide sequence shown in SEQ ID No.: 1, 3 or 5.

Another preferred embodiment includes a polynucleotide having a nucleotide sequence with at least 70%, preferably at least 80%, more preferably at least 90%, most preferably 100%, homology to the nucleotide sequence shown in SEQ ID No.: 1, 3 or 5.

The polynucleotide may further comprise a sequence encoding a signal peptide. The signal peptide is an amino acid sequence which initiates transport of a protein across the membrane of the endoplasmic reticulum. Suitable signal peptides will be known to one skilled in the field of the invention.

The invention also includes peptides encoded by a polynucleotide sequence of the invention.

According to other aspects of the present invention there is provided an expression system comprising a polynucleotide sequence of the invention, and a host cell transformed by said expression system capable of expressing a protein or peptide of the invention.

The invention also includes methods of making a peptide or protein of the invention, said method including the steps of
(i) preparing a replicable expression system capable, in a host cell, of expressing a nucleotide sequence that encodes a protein or peptide of the invention;
(ii) transforming a host cell with said expression system;
(iii) culturing said transformed host cell under conditions permitting expression of said protein or peptide; and
(iv) optionally, recovering said protein or peptide.

The invention also comprises transgenic animals capable of producing a protein or peptide of the invention, for example in their milk or in the white of their eggs.

According to another aspect of the present invention, there is provided the use of a protein or peptide of the invention for the treatment of an immunological disorder, particularly a hypersensitivity disorder such as allergy.

According to a further aspect of the present invention, there is provided the use of a protein or peptide of the invention for the preparation of a medicament for the treatment of an immunological disorder, particularly a hypersensitivity disorder such as allergy. Preferably the medicament is a vaccine.

Preferably the hypersensitivity disorder is an allergy to *Parietaria* pollen, more preferably *Parietaria judaica* pollen.

As used herein, the term treatment and variations such as 'treat' or 'treating' refer to any regime that can benefit a human or non-human animal. The treatment may be in respect of an existing condition or may be prophylactic (preventative treatment). Treatment may include curative, alleviation or prophylactic effects. Preferably the treatment is prophylactic treatment.

According to yet a further aspect of the present invention there is provided a pharmaceutical composition comprising an effective amount of a protein or peptide of the invention and a pharmaceutically acceptable excipient. Preferably the pharmaceutical composition is a vaccine composition.

According to a yet still further aspect of the present invention there is provided a method of treating an immunological disorder, particularly a hypersensitivity disorder such as allergy, said method comprising the step of administering an effective amount of a protein or peptide of the invention to a subject in need thereof.

According to another aspect of the present invention there is provided a protein or peptide of the invention for use in the treatment of an immunological disorder, particularly a hypersensitivity disorder such as allergy.

The selection of the appropriate administration and dosage forms for an individual patient will be apparent to those skilled in the art.

The present invention covers the use of the chimeras according to the present invention, preferably the chimera Q2, or synthetic peptides derived therefrom for desensitisation treatments in mammals. Desensitisation methods involve the repeated administration by parenteral routes (subcutaneous, intravenous, or intramuscular), or oral, nasal or rectal routes of the allergen in question. These (poly)peptides can be administered either alone or in combination with other diluents, in accordance with the prevailing legislation and the galenical procedures for use.

Figure 13:
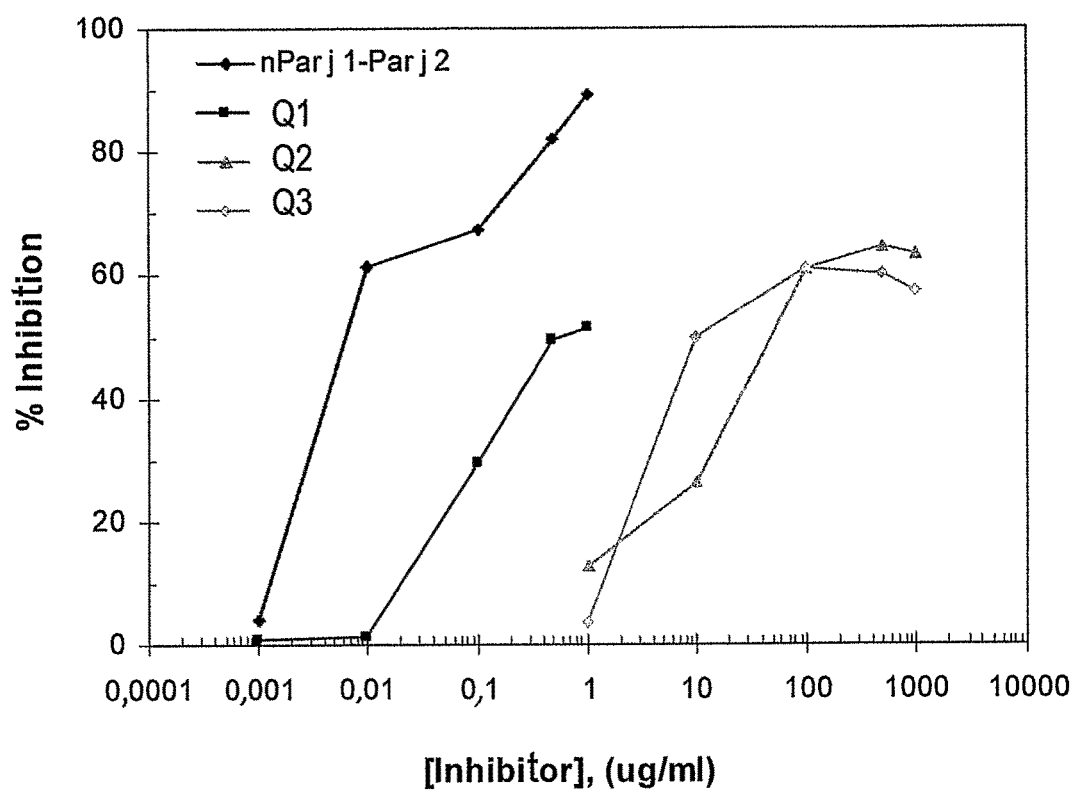
FIG. 13 shows an ELISA inhibition test result using *P. judaica* extract in the solid phase and nPar j 1-Par j 2, Q1, Q2, and Q3 as inhibitors using a mixture of sera of patients allergic to *P. judaica*. Each value corresponds to the mean of three experiments with a standard deviation of less than 10%.

The chimeric proteins Q2 and Q3 described in the invention are hypoallergenic since, as shown in FIGS. 10, 11, 12 and 14, they have lower reactivity to the serum of patients allergic to *P. judaica* than the complete extract or the combined natural proteins, and, moreover, this hypoallergenicity is also found in in vivo cutaneous tests (FIG. 13).

Figure 16:
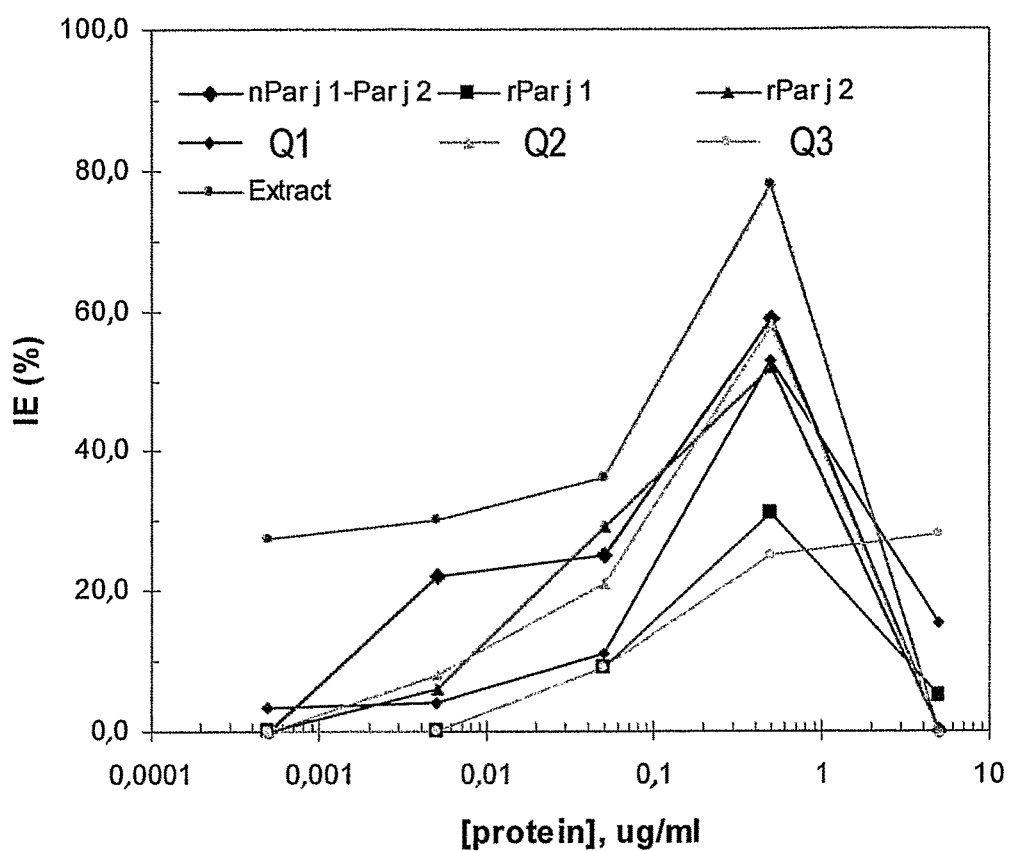
FIG. 16 shows a determination of the optimum concentration for studying the proliferation of T lymphocytes in patients allergic to *P. judaica*. Stimulation index (IE).

The chimeric molecules Q1 and Q2 also have an immunogenic capacity similar to that of the combined natural proteins (FIG. 16). Both characteristics (hypoallergenicity and immunogenicity) make the chimera Q2 an excellent candidate for the preventive and curative treatment of the allergy to *P. judaica* pollen which can be manifested as rhinitis, conjunctivitis, asthma, urticaria, angioedema, eczema, dermatitis, or even anaphylactic shock.

Figure 10:
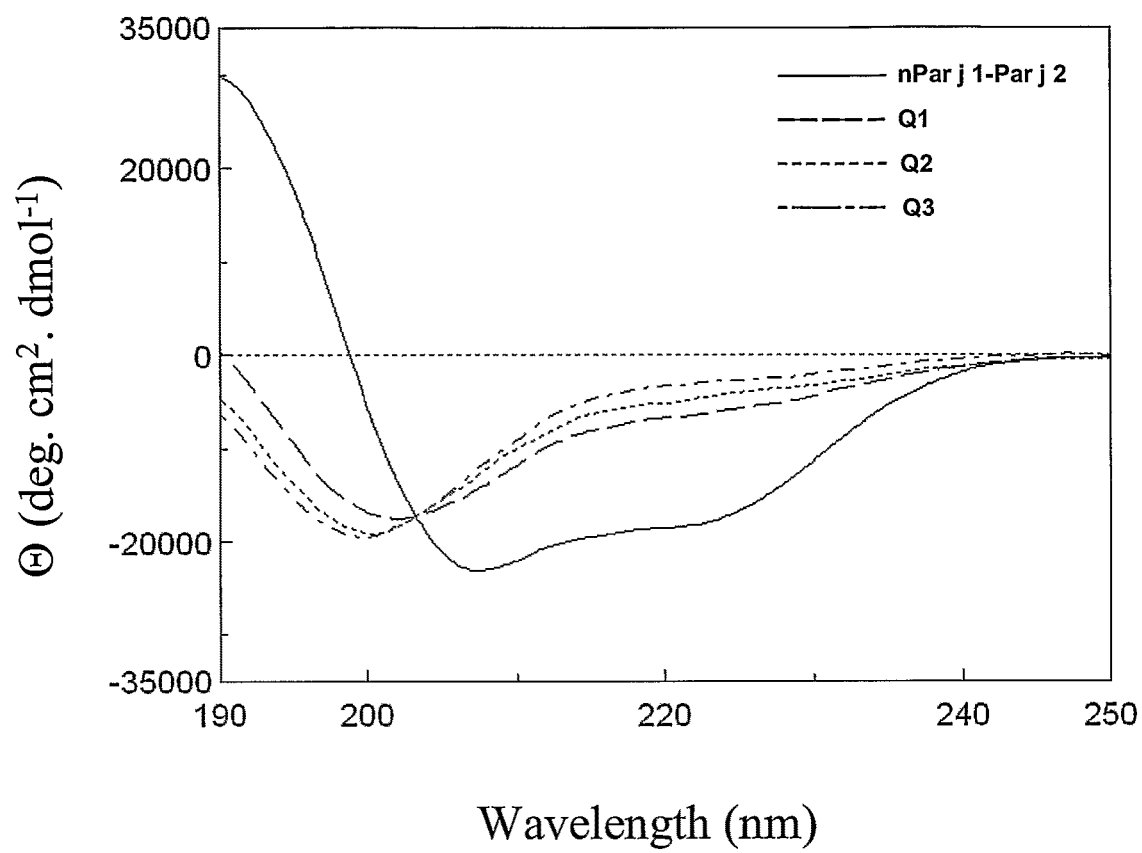
FIG. 10 shows the results of a Circular dichroism analysis of the purified proteins nPar j 1-nPar j 2, Q1, Q2, and Q3.
Figure 11:
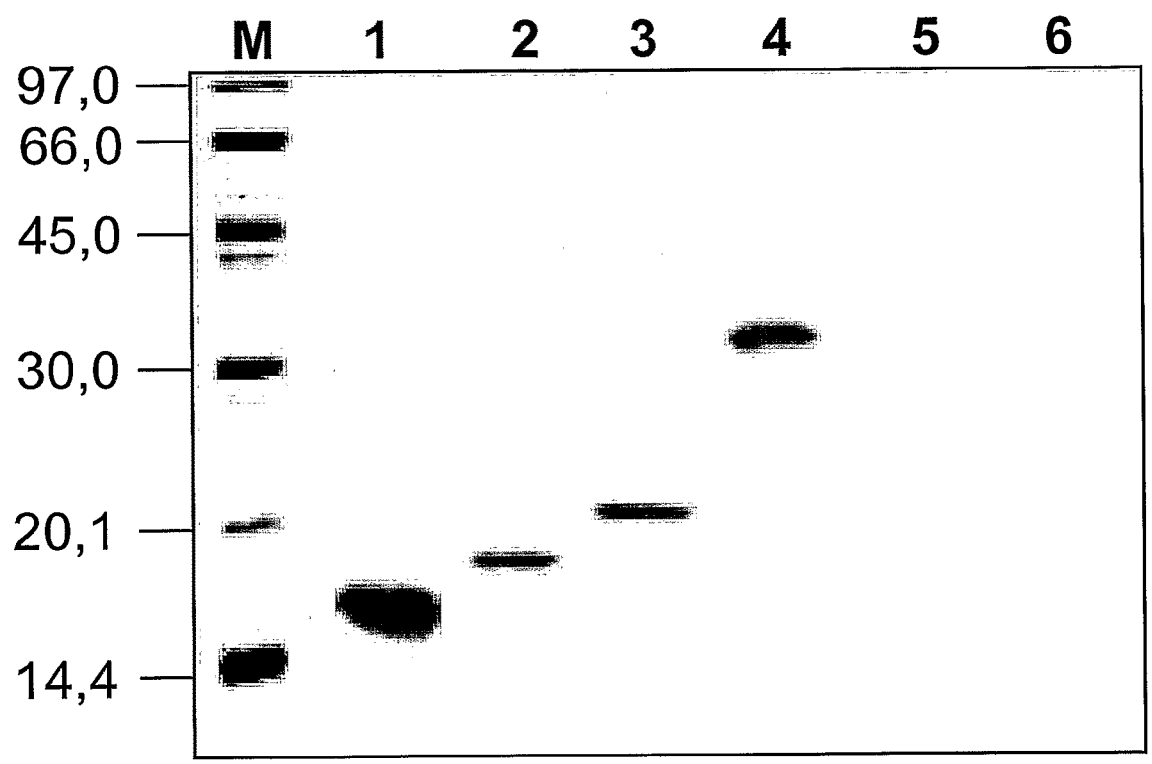
FIG. 11 shows immunodetection with IgE antibodies of a mixture of sera of patients allergic to *P. judaica* comprising: nPar j 1-nPar j 2 (lane 1), rPar j 1 (lane 2), rPar j 2 (lane 3), Q1 (lane 4), Q2 (lane 5), Q3 (lane 6).
Figure 12:
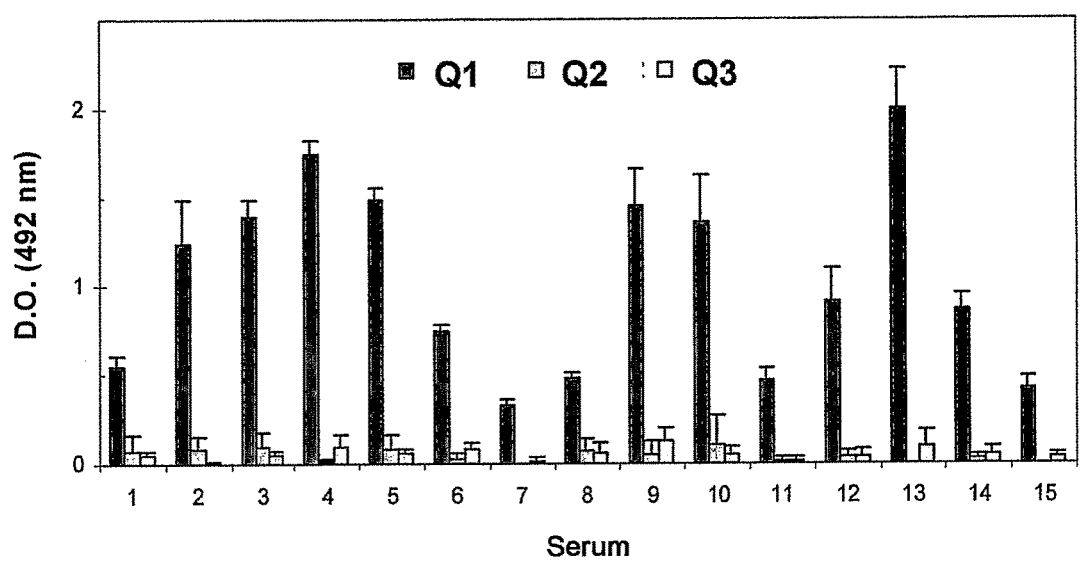
FIG. 12 shows a binding of IgE antibodies to Q1, Q2, and Q3 using 15 sera from patients allergic to *P. judaica* (dilution 1/10). The values of three experiments are shown with their deviations.

The immunological characteristics of the chimeric protein according to the present invention will be described hereinafter. FIG. 10 shows an immunodetection test which indicates that the chimeras Q2 and Q3 (lanes 5 and 6) have a greatly reduced IgE-binding capacity in allergic patients when compared with the reactivity of the two natural proteins (lane 1), the isolated recombinant proteins (lanes 2 and 3) or the chimera (lane 4), which shows the recombinant fusion of the two proteins which are complete but contain all their B epitopes. This should indicate that the absence of the B epitopes included between the residues 29 and 52 (chimera Q2) contributes to the reduction in allergenicity. A similar result was obtained when the reactivity of 15 different sera toward the chimeric proteins was investigated (FIG. 11). The chimeric proteins Q2 and Q3 have much lower reactivity than that observed for Q1, which is the binding of the two complete allergens (Par j 1-Par j 2). This reduction in the allergenicity was quantified by ELISA inhibition with a mixture of sera from patients allergic to *P. judaica* (FIG. 12). 10,000 times more protein Q2 was required to reach the 60% inhibition of the extract than of the mixture of the two natural proteins. It could therefore be inferred that it was 10,000 times less allergenic than the natural proteins and about 20 times less allergenic than the chimeric protein Q1.

A more direct measurement of the hypoallergenicity of the chimera Q2 was obtained by direct measurement of cutaneous reactivity in 30 patients allergic to *P. judaica* pollen. The data given in FIG. 13 shows that the chimera Q2 had a marked reduction in cutaneous reactivity. A comparison of the descriptives of each distribution shows that the chimera Q2 has an average size of patches 112 times smaller than that observed for the two natural proteins, and this indicates a reduction in the allergenic activity by more than 99%.

Figure 14:
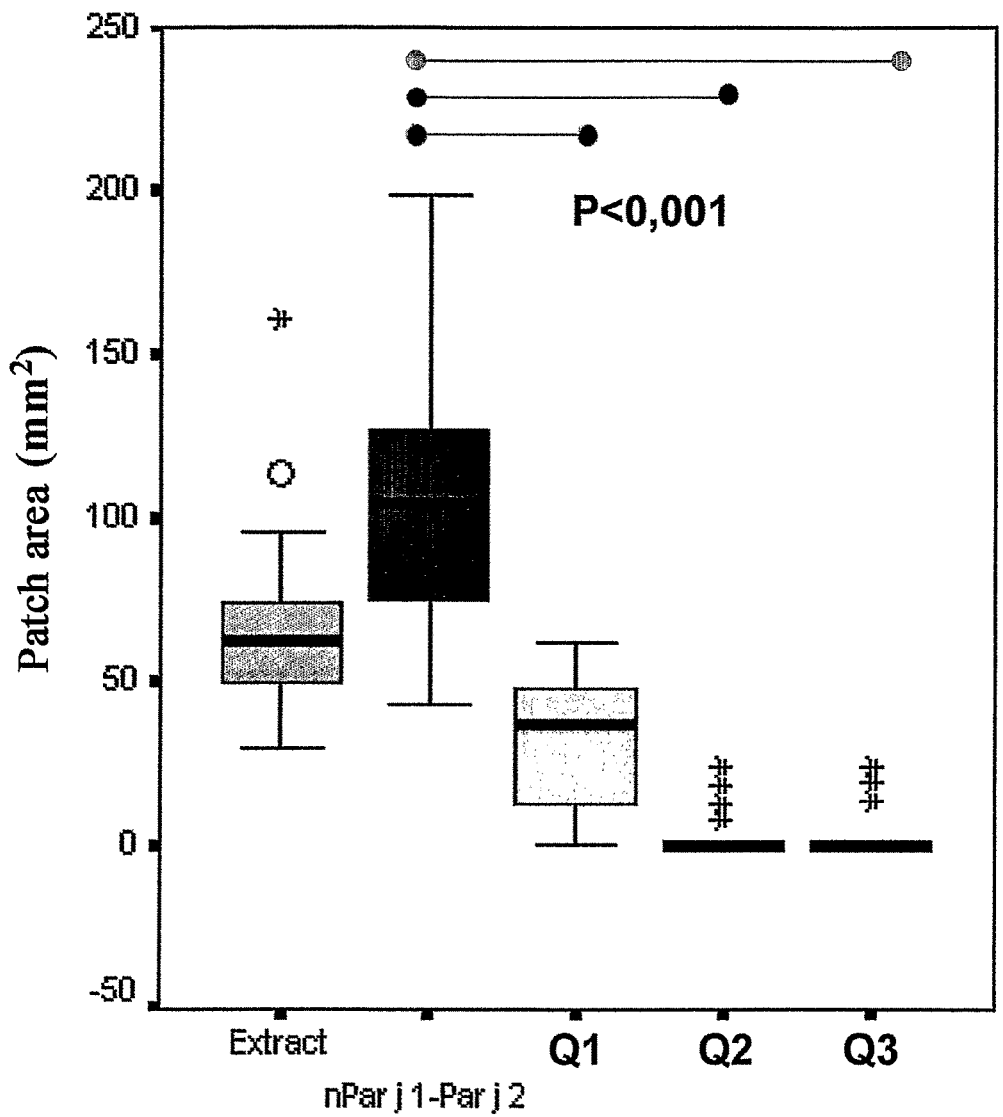
FIG. 14 shows the result of cutaneous tests carried out with extract of *P. judaica*, nPar j 1-Par j 2 and Q1 (50 µg/ml), and Q3 (250 µg/ml). The value shown is the area of the patch in $mm^2$.

The low binding capacity of IgE with the chimeric protein Q2 was also demonstrated with the serum from a further 30 patients allergic to *P. judaica* measured by EAST (FIG. 14). In all the patients, the IgE-binding was greatly reduced in the chimera Q2 compared to the mixture of natural proteins.

This great reduction in the IgE-binding capacity and therefore in the capacity to trigger adverse reactions owing to the deletion of B epitopes was accompanied by maintenance of the immunogenic capacity. The protein Q2 demonstrated a lymphoproliferation index which was similar to that induced by the natural extract and the mixture of the two pure natural proteins combined, as shown in FIG. 16. All this shows that the chimeric protein Q2 constructed with fragments of Par j 1 and Par j 2 contained a smaller number of IgE epitopes but maintained sufficient T epitopes to induce a protective immune response.

The invention will be understood better by means of the following examples relating to experimental stages in the preparation of the invention and demonstration of its qualities. These examples are merely illustrative examples and do not limit the invention.

EXAMPLE 1

Construction of the Q1, Q2, and Q3 Fusions

The chimeric proteins were constructed by chain amplification of the polymerase (PCR) using, as a matrix, plasmids containing the sequences coding for Par j 1.0103 and Par j 2.0101 described in Gonzalez-Rioja et al., "Expression and purification of the recombinant allergens Par j 1 and Par j 2" XXIII Congreso EAACI, Abstracts Book (2004), 181-182 and specific triggers in each case. The triggers are composed of the hybridation zone, of various section sites for differing restrictive endonucleases (underlined), and of some anchoring nucleotides. The PCR-induced amplification reaction had the following components in a reaction volume of 50 µl: amplification buffer x10, 5 µl; 200 µM of dNTPs; 100 pmoles of each triggering oligonucleotide: 2.5 units of polymerase Taq (Pfx DNA polymerase, Invitrogen); 1 ng DNA matrix and sterile distilled water to 50 µl. The amplification reaction was carried out in a ROBOCYCLER thermocycler (Stratagene) under specific conditions which will be described in each case. The reaction product was subjected to electrophoresis in agarose gel (2%) and the band of interest was isolated from the gel using GENECLEAN DNA purification kit (Bio101), using the method described by the manufacturer. The isolated fragments were digested by appropriate restrictive enzymes and bound to the pBluescript vector digested by the same enzymes. The ligation mixture was used to transform competent cells of *E. coli* DH5a (obtainable from Invitrogen, Paisley, UK). The resultant colonies were grown in order to isolate their plasmid DNA, which was digested by the appropriate enzymes in order to liberate the fragment of interest. The positive clones were selected for the sequencing thereof. The sequencing of the DNA inserted the pBluescript was carried out by Sanger's method [(30) Hanahan, D. (1983). Studies on transformation of *Escherichia coli* with plasmids. J. Mol. Biol. 166, 557-580] modified for use with fluorescent dideoxynucleotides and amplification in a thermocycler using PRISM Ready Reaction DiDeoxy Termination Cycle Sequencing Kit (Perkin Elmer), following the manufacturer's instructions.

A) Chimeric Protein Q1

In this case, the complete sequences of both proteins (Par j 1 and Par j 2) were to be fused in order to obtain a protein having the destabilised tertiary structure but with all its sequential IgE epitopes complete. In order to obtain the construction known as Q1, the cDNAs of Par j 1 and Par j 2 cloned in the vector pKS-Bluescript were used as matrices. For fusing the two sequences, it was necessary to have a linker, in this case EcoRI target, both in the C-terminal end of the sequence of Par j 1 and in the N-terminal end of Par j 2, to allow the subsequent ligation of the fragments. Said target was added to the corresponding synthetic oligonucleotide (F1R1 and F1F2), and was incorporated in the amplified fragment in the PCR process.

Synthetic oligonucleotides used:

X Fragment 1: F1F1, CG GGATCC TGCAAGAAACCT-GCGG (HamHI) (SEQ. ID NO.: 7) and F1R1, CG GAATTC GGCTTTTTCCGGTGCGG (EcoRI) (SEQ. ID NO.: 8). Conditions: 94° C., 4 min (1 cycle); 94° C., 30 s—53° C., 30 s—72° C., 90 s (5 cycles); 94° C., 30 s—60° C., 30 s—72° C., 90 s (35 cycles); 72° C., 10 min (1 cycle).

X Fragment 2: F1F2, CG GAATTC GAGGAGGCT-TGCGGGA (EcoRI) (SEQ ID NO.: 9) and F1R2, CG AAGCTT CTAATAGTAACCTCTGA (HindIII) (SEQ. ID NO.: 10). Conditions: 94° C., 4 min (1 cycle); 94° C., 30 s—51° C., 30 s—72° C., 90 s (5 cycles); 94° C. 30 s—59° C., 30 s—72° C., 90 s (35 cycles); 72° C., 10 min (1 cycle).

Two products of PCR corresponding to Par j 1 and Par j 2 respectively were created. For the first of them (Par j 1), the synthetic oligonucleotides F1F1 and F1R1 were used for the N and C terminal ends respectively, a size of approximately 420 pairs of bases (pb) being obtained. The amplified fragment was cloned in the pKS-Bluescript vector and its sequence was confirmed. For the second fragment corresponding to Par j 2, the same procedure was employed using the oligonucleotides F1F2 and F1R2 for the N and C terminal ends respectively. On this occasion, a fragment of approximately 300 pb was obtained, which was cloned in the pKS-Bluescript vector and of which the sequence was confirmed. This second fragment was bound to the first by ligation through the EcoRI target, Par j 1 remaining at the N-terminal end and Par j 2 at the C-terminal end, and the resultant fragment was subsequently subcloned in the commercial expression vector pQE-32 (Qiagen), containing an extra sequence of 13 amino acids at the N-terminal end, corresponding to the affinity tail (FIG. 2). Said sequence coded for a polypeptide having 256 amino acids and an apparent molecular weight of 28070 Da.

B) Chimeric Protein Q2

Figure 3:
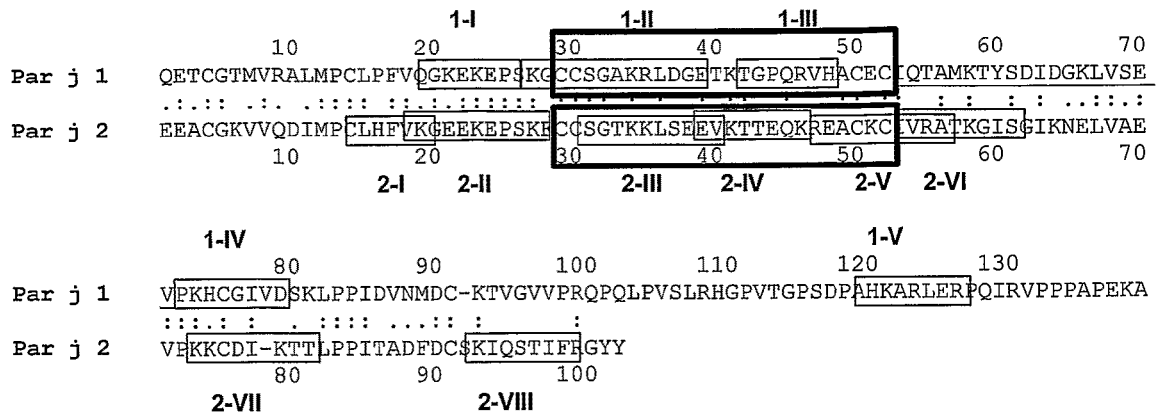
Figure 4:
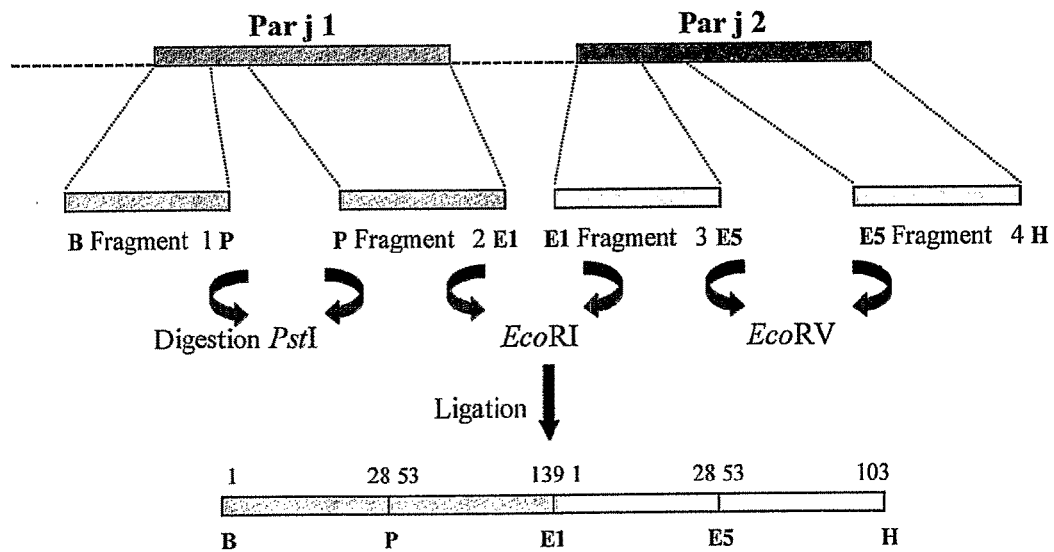
FIG. 4 is a constructional diagram of Q2.

When obtaining this chimera, the fragment of both proteins was to be bound but without including any of the described sequential IgE epitopes [(18) Asturias, J. A, Gómez-Bayón, N., Eseverri, J. L., and Martinez, A. (2003). Par j 1 and Par j 2, the major allergens from *Parietaria judaica* pollen, have similar immunoglobulin E epitopes. Clinical and Experimental Allergy 33, 518-524]. Some synthetic oligonucleotides which comprised the following fragments were designed: Par j 1 (fragments of the residue 1 to 28 and 53 to 139) and Par j 2 (fragments of the residue 1 to 28 and 53 to 103) (FIGS. 3 and 4). Part of the sequence containing the IgE epitopes was eliminated in this way.

Four fragments (two for each allergen) were amplified for this construction and the cDNA of Par j 1 and Par j 2 cloned in the pKS Bluescript vector was used as the matrix. The construction mechanism of the new protein is the use of restrictive enzymes (PstI, EcoRi and EcoRV in this case) for the sequential binding of the differing amplified fragments.

Synthetic oligonucleotides used:

X Fragment 1: F1F1, CG GGATCC TGCAAGAAACCT-GCGG (BamHI) (SEQ. ID NO. 72) and F2R1, CG CTGCAG CCCCTTTGACGGCTCTT (PstI) (SEQ. ID NO.: 11). Conditions min (1 cycle); 94° C., 30 s—54° C., 30 s—72° C., 90 s (35 cycles); 72° C., 10 min (1 cycle).

X Fragment 2: F2F2, CG CTGCAG ATCCAGACCGC-CATGAA (PstI) (SEQ. ID NO.: 12) and F2R2, CG GAATTC GGCTTTTTCCGGTGCGGG (EcoRI) (SEQ. ID NO.: 13).

X Fragment 3: F2F3, CG GAATTC GAGGAGGCT-TGCGGGAA (EcoRI) (SEQ. ID NO.: 14) and F2R3, CG GATATC CTCCTTCGACGGCTCCTT (EcoRV) (SEQ. ID NO.: 15).

X Fragment 4: F2F4, CG GATATC ATAGTGCGCGC-CACGAA (EcoRV) (SEQ. ID NO.: 16) and F1R2, CG AAGCTT CTAATAGTAACCTCTGA (HindIII) (SEQ. ID NO.: 10). The conditions of the three fragments were: 94° C., 4 min (1 cycle; 94C, 30 s—54° C., 30 s—72° C., 90 s (5 cycles); 94° C., 30 s—62° C., 30 s—72° C., 90 s (35 cycles); 72° C., 10 min (1 cycle).

For the first of these, corresponding to Par j 1 (fragment 1), the synthetic oligonucleotides F1F1 and F2R1 were used for the N and C terminal ends respectively, a size of approximately 90 base pairs being obtained and cloned in the pKS-Bluescript vector. For the second fragment corresponding to Par j 1, the same procedure was carried out using the oligonucleotides F2F2 and F2R for the N and C terminal ends respectively. On this occasion, a fragment of approximately 260 pb was obtained and was cloned in the pKS-Bluescript vector. This last fragment was bound to the first by ligation through the linker of the target carried by PstI and its sequence was confirmed.

With regard to the two fragments amplified from the sequence of Par j 2 (fragments 3 and 4, the procedure described for fragments 1 and 2 was followed. The oligonucleotides F2F3/F2R3 and F2F4/F1R4 for the N and C terminal ends respectively were used for the amplification thereof, the size of the products of PCR being approximately 90 and 150 pb for fragments 3 and 4. Fragment 4 was bound to fragment 3 by ligation through the linker of the target carried by EcoRV and its sequence was confirmed.

In a last step, the two new fragments created (one for each allergen) were bound by ligation via the linker of the target carried by EcoRI, Par j 1 remaining at the N-terminal end and Par j 2 at the C-terminal end. Said fragment was subsequently subcloned in the commercial expression vector pQE-32, containing an extra sequence of 13 aminoacids at the N-terminal end corresponding to the affinity tail (FIG. 5). Said sequence coded for a polypeptide having 212 aminoacids and an apparent molecular weight of 23336 Da.

C) Chimeric Protein Q3

Figures 6, 7:
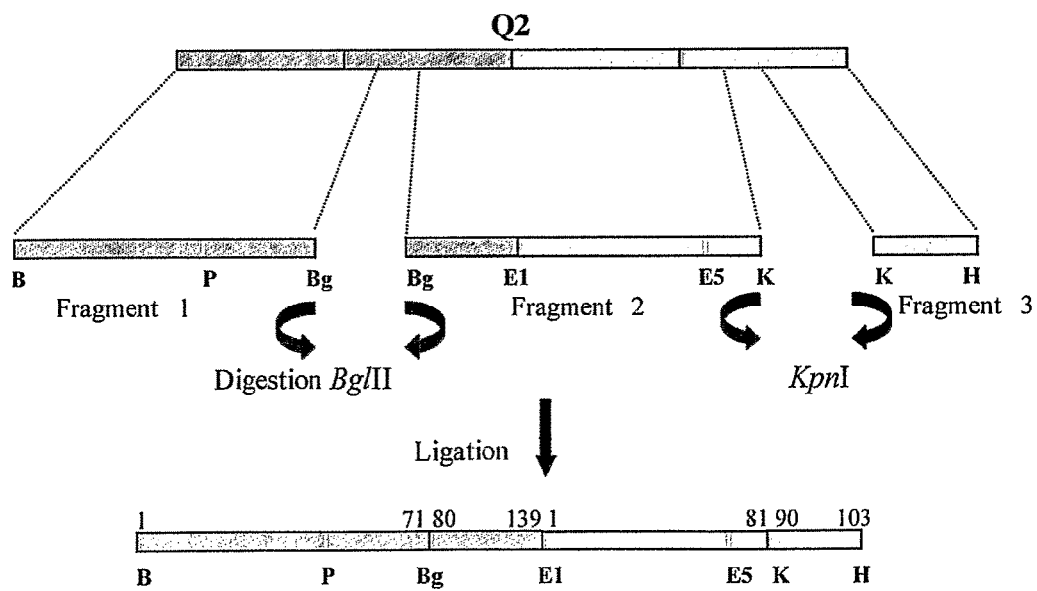
FIG. 6 shows a comparison of the IgE epitopes of Par j 1 and Par j 2 (boxes) and the T epitope (underlined), indicating the Q3 deleted epitopes in double-lined boxes. The identical residues (:) and similar residues (.) have been labeled.
FIG. 7 is a constructional diagram of Q3.

This last construction was virtually identical to Q2 except that on this occasion and in an attempt to eliminate any possible existence of IgE epitopes, another additional sequence of 8 aminoacids present in the sequences of Par j 1 (residue 71 to 80) and Par j 2 (residue 72 to 81) (FIGS. 6 and 7) was eliminated.

Synthetic oligonucleotides used:

X Fragment 1: F1F1, CG GGATCC TGCAAGAAACCT-GCGG (BamHI) (SEQ. ID NO.: 7) and F3R1, CG AGATCT GACCTCGCTGACGAG (BglII) (SEQ. ID NO.: 17).

X Fragment 2: F3F2, CG AGATCT AGCAAGCTC-CCGCCC (BglII) (SEQ. ID NO.: 18) and F3R2, CG GGTACC GGGGACCTCGGCGAC (KpnI) (SEQ. ID NO.: 19). The conditions of the 2 fragments were: 94° C., 4 min (1 cycle); 94° C., 30 s—54° C., 30 s—72° C., 90 s (5 cycles); 94° C. 30 s—63° C., 30 s—72° C., 90 s (35 cycles); 72° C., 10 min (1 cycle).

X Fragment 3: F3F3, CG GGTACC CTCCCGCCCAT-CACC (KpnI) (SEQ. ID NO.: 20) and F3R3, TTTAAAAAG-GCCGTAATATCC (SEQ. ID NO.: 21). Conditions: 94° C., 4 min (1 cycle); 94C, 30 s—56° C., 30 s—72° C., 90 s (35 cycles); 72° C., 10 min (1 cycle).

In this case, the construction Q2-pQE-32 was used as the matrix and approximately 150, 370 and 290 pb in size were obtained for the fragments 1, 2 and 3 respectively. The oligonucleotides used were F3F1 and F3R1 for the fragment 1, F3F2 and F3R2 for the fragment 2, and F3F3 and F3R3 for the fragment 3. The processes of sequential ligation of the fragments described in the earlier cases was repeated again. The new restrictive enzymes used were BglII and KpnI. In the third and last fragment and owing to the smallness of its size, 66 pb, it was decided to amplify part of the sequence of the vector pQE-32-Q2 in order to obtain a fragment of greater size in order to be able to work with greater convenience in the subsequent purification process. At each step, the fragment obtained by PCR cloned in the vector pKS-Bluescript and its sequence was confirmed. A spontaneous mutation in the first fragment corresponding to the first glutamine amino acid (Q) was produced by proline (P).

Finally, the resultant fragment subcloned in the expression vector pQE-32, containing an extra sequence of 13 amino acids at the N-terminal end corresponding to the affinity tail (FIG. 8). Said sequence coded for a polypeptide having 200 amino acids and an apparent molecular weight of 21938 Da.

EXAMPLE 2

Expression and Purification of the Chimeric Proteins Q1, Q2, and Q3

Starting from a colony isolated from a sheet of LB (supplemented with 100 and 25 μg/ml of ampicillin and kanamycin respectively), a pre-inoculum of 50 ml of the same medium was produced and incubated overnight at 37° C. with stirring (260 rpm). One liter of the same medium was inoculated with said pre-inoculum, starting from an optical density (600 nm) of 0.2. The mixture was incubated at 37° C. with stirring for 1 hour and 30 minutes, after which induction with a IPTG (1 mM of final concentration) was carried out for 3 h under the same incubation conditions.

In the case of Q2, the cells were centrifuged at 10,000 rpm for 15 minutes at 4° C. and were resuspended in 50 ml of lysis buffer (phosphate 20 mM, pH 7.4; 50 mM imidazole; 0.5 M NaCl). The resuspended matter was treated with lysozyme (final concentration of 0.1 mg/ml) for 30 minutes at 37° C. with stirring. Sonication (5 pulses of 20 s) was then carried out and the mixture was centrifuged at 15000 rpm for 15 minutes at 4° C. The supernatant was filtered over 0.45 pm (Millex HV, Millipore) and was applied (2.5 ml/min) to a 5 ml HI-TRAP Chelating HP column (GE-Healthcare) adapted to the AKTAPRIME chromatography system (GE-Healthcare). This column was chelated with nickel and had previously been balanced with 10 volumes of the lysis buffer. Once the column had been washed with 15 volumes of lysis buffer, elution of protein bound to the column was carried out using elution buffer (phosphate 20 mM pH 7.4; 0.5 M imidazole) to 100%. The elute was passed through a 5 ml HI-TRAP Desalting column (GE-Healthcare) in order to remove salts and change the 20 mM pH 7 phosphate buffer sample. The protein was kept at −40° C.

An additional purification step was required in the cases of Q1 and Q3. After the induction thereof, the cells were centrifuged at 10,000 rpm for 15 minutes at 4° C. and were resuspended in 50 ml of lysis buffer supplemented with 8 M of urea, the procedure described in the preceding paragraph being adopted. In a second purification step, the elute obtained was applied (1 ml/min) to a HI-LOAD 16/60

SUPERDEX-200 protein purification column (GE-Healthcare) previously balanced with PBS; elution of the protein was carried out in the buffer described in the preceding paragraph. The protein was kept at −40° C.

Electrophoresis was carried out in polyacrylamide gels with SDS (SDS-PAGE). The method described by Laemmli was basically followed [(31) Laemmli, U. K. (1970). Cleavage of structural proteins during the assembly of the head of bacteriophage $T_4$. Nature 277, 680-685], using a MINI-PROTEAN electrophoresis apparatus (Bio-Rad). The gels, measuring 10×10 cm and having a polyacrylamide concentration of 12.5% were subject to a 200 volt current for 45 minutes in tris-glycine buffer. The proteins used as a reference were those from the Bio-Rad kit for low molecular weights. Calculation of the molecular weights and densitometric analysis of the gels were carried out using an image analyser (Diversity, BioRad).

Figure 9:
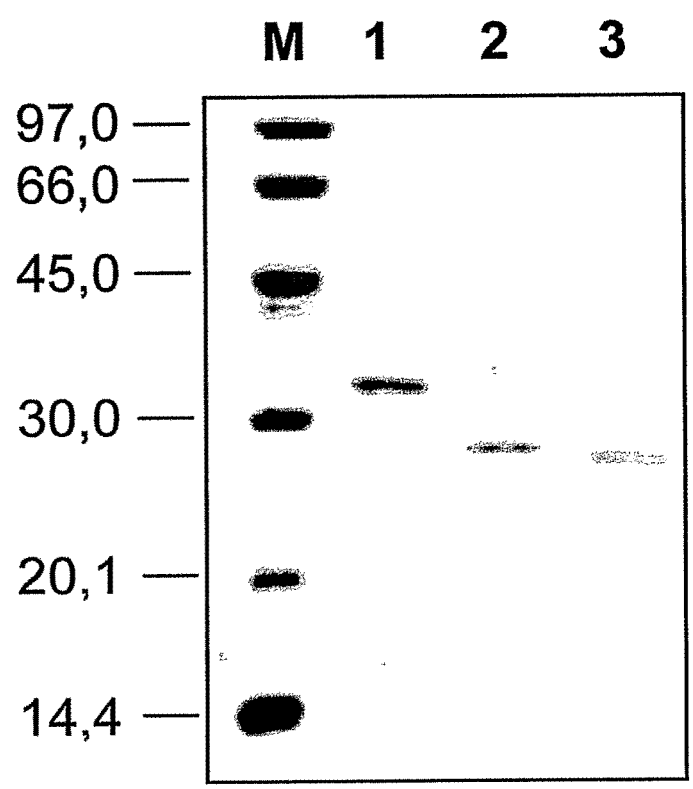
FIG. 9 shows staining by Coomassie blue of a polyacrylamide gel after electrophoresis: Q1 (lane 1), Q2 (lane 2), Q3 (lane 3).

Hybrid protein Q1 was expressed as 32 kDa His-tagged fusion protein (FIG. 9) with a final yield of 2 mg/L of bacterial culture. Q2 and Q3 proteins were expressed as 28 kDa His-tagged fusion proteins with a final yield of 5 and 7 mg/L culture, respectively (FIG. 9).

EXAMPLE 3

Circular Dichroism Analysis of the Purified Hybrid Molecules

Far-UV (190-250 nm) CD spectra at pH 7.0 and 20° C. were recorded with a Jasco J-810 spectropolarimeter equipped with a Jasco PTC-423S temperature controller in cuvettes thermostatted at 20° C. Protein concentration was 0.035 mg/ml in 20 mM sodium phosphate buffer in a 0.2 cm cuvette and forty scans were accumulated. All the spectra were subtracted by the appropriate background and converted to mean residue ellipticity.

Secondary structure elements were analyzed by CD spectroscopy applying natural *Parietaria* allergens mix (Par j 1 and Par j 2) and the hybrid proteins (FIG. 10). The spectra of the hybrid proteins were nearly identical among them but totally different from the natural allergens CD spectra. NPA spectra presented a minimum at 208 nm, a well defined shoulder at 222 nm and a maximum at 190 mm, whereas spectra of the hybrid proteins shifted towards random coil conformation reaching an almost completely unfolded state.

EXAMPLE 4

Immunological Tests to Demonstrate the Low Ige-Fixing Reactivity of Chimeric Proteins Toward a Mixture of Sera of Patients Allergic to *P. judaica*

A) Immunodetection

A first evaluation of the IgE-binding activity of the fusions 1, 2 and 3 was carried out by the immunotransfer method employing a mixture of sera from patients allergic to *P. judaica*. Once the protein extracts and the purified proteins had been applied to polyacrylamide gels, electrotransfer was carried out by the method of Towbin et al [(32) Towbin, H., Staehelin, I., and Gordon, J. (1979). Electrophoretic transfer of proteins from polyacrylamide gels to nitrocellulose sheets: Procedure and some applications. Proc. Natl. Acad. Sci. USA 76, 4350-4354]. For this purpose, the proteins separated by SDS-PAGE were electrically transfixed to PVDF HYBOND-P membranes (GE-Healthcare). Once the membranes had been blocked for 1 h at ambient temperature, they were incubated overnight at 4° C. with a primary antibody and, after the various washes with the same washing buffer, the membranes were incubated for 1 h at ambient temperature with a secondary peroxydase conjugate antibody. Bands were detected by the ECL chemiluminescent method (GE-Healthcare) as described by the manufacturer by exposing the membrane to a film (Hyperfilm.ECL, GE-Healthcare).

The immunodetection tests demonstrated a different IgE-binding capacity between the three fusions; recognition of IgE antibodies accordingly existed only in the case of Q1 (FIG. 11). In the case of Q2, recognition dropped very sharply, while in the case of Q3, the demonstrated recognition was zero.

B) Direct ELISA

The reactivity of IgE to the three fusions was analysed by the ELISA method using individual sera from patients allergic to *P. judaica*. The polystyrene plates (Greiner) were incubated overnight at ambient temperature with 1 μg of *P. judaica* extract protein or 0.1 μg of pure protein per cup in PBS buffer (phosphate 10 mM pH 7.2; 137 mM NaCl 2.7 mM KCl). They were blocked with 200 μl/cup of PBS supplemented with 1% BSA-0.05% TWEEN 20 (polyoxyethylene sorbitan monolaurate) and kept at 37° C. for 1 h. 100 μl/cup of serum (dilution 1/10) from allergic patients were added and incubated at 37° C. for 90 min. After 3 washes with 200 μl/cup of PBS-T (PBS+0.05% TWEEN 20 (polyoxyethylene sorbitan monolaurate)), 100 μl/cup of an antiserum toward human IgE immunoglobulins (Dako) conjugated with peroxidase were then added (dilution 1:1000) and were incubated for 90 min at 37° C. After three new washes with PBS-T, 200 μl/cup of a solution of o-phenylenediamine (SIGMAFAST Tablet Sets, Sigma) prepared in accordances with the manufacturer's instructions were added and the plates were kept in darkness for 30 minutes. The reaction stopped with 50 μl/cup of 3 M $H_2SO_4$ and the absorbency was measured at 492 nm in an ELISA Easy Reader EAR-400 AT (SLT-Lab Instruments) plate reader.

The reactivity to IgE was demonstrated only in the case of the Q1, while both the Q2 and the Q3 demonstrated virtually no recognition of the Ige antibodies (FIG. 12).

C) ELISA Inhibition

For the ELISA inhibition tests, the mixture of sera from patients allergic to *P. judaica* was preincubated overnight at 4° C. with a given concentration of inhibiting protein (from 1 to 1000 ng/ml). The remainder of the procedure followed is the same as described for the ELISA direct test.

In ELISA-inhibition tests with a mixture of sera from patients allergic to *P. judaica*, Q1 demonstrated a degree of inhibition of about 50% of the IgE-binding activity of the *P. judaica* pollen, some what lower than that of nPar j 1-Par j 2 (92%), it being necessary to add 500 times more protein (FIG. 13). The chimeras Q2 and Q3 reached a maximum degree of inhibition of about 60%, but this required a protein concentration 10,000 times higher than that of required for nPar j 1-Par j 2 in order to reach the same degree of inhibition, which implied that these chimeras had reduced their allergenicity by about 99.99%.

EXAMPLE 5

In Vivo Experiments to Demonstrate the Low Cutaneous Reactivity of the Chimeric Proteins Q1, Q2, and Q3

In vivo skin reaction (prick) tests were carried out to evaluate the hypoallergenic nature of the chimeras 1, 2 and 3 with the aim of determining the candidate hypoallergenic molecule in order to be able to develop satisfactory immunotherapy against the allergy to *P. judaica* pollen.

The cutaneous tests were carried out using *P. judaica* extract, nPar j 1-Par j 2, rPar j 1 and rPar j 2 expressed in *E. coli*, and the chimeras 1, 2 and 3. The purified proteins were diluted in a 0.5% phenolated and 50% glycerinated physiological saline solution. The concentrations used were 0.5, 5, and 50 µg/ml in the case of natural Par j, Par j 2, Q1; the concentrations were 5, 50 and 250 µg/ml in the case of Q2 or Q3. 0.9% NaCl and histamine hydrochloride (10 mg/ml) were used as negative and positive controls respectively.

In the experiment a droplet of each allergen to be tested was deposited on the volar zone of the forearm, and the puncture was then made through the droplet with a lancet. Each test was carried out in duplicate and in opposing strings of increasing and decreasing concentration. After a period of 15 min, the patches were outlined with a fine-pointed black marker pen. Strips of hypoallergenic sticking plaster were placed on the patches and were pressed gently to pass the ink marking to the strip; this was transferred to the patch record sheets. The patch areas were measured by scanning the records using a Summasketch digitising tablet and a computer assisted design program (Autocad v.11).

The results obtained were interpreted by carrying out a statistical survey by illustrating the results in block diagrams and using the Wilcoxon test for the related variables (FIG. 14). These illustrations show that distributions of the values corresponding to the cutaneous reactions (measured in $mm^2$ of patch area) differ significantly in the case of the three chimeras (P<0.001) with respect to the extract (mean 65.25 $mm^2$-confidence range 95%:54.98-75.53) and nPar j 1-Par j 2 (mean 106.80 $mm^2$-confidence range 95%:91.90-121.70). The values for the chimeras 2 and 3 are virtually zero: Q2 (mean 0.95 $mm^2$-confidence range 95%:0-2.89) and Q3 (mean 0.15 $mm^2$-confidence range 95%:0-0.47).

EXAMPLE 6

Experiments to Demonstrate the Low Ige Antibody-Binding Capacity of the Chimeric Proteins Q1, Q2, and Q3

Anew, as a supplement to the in vivo tests, in vitro tests were carried out by determining specific IgE, using the EAST-direct method.

The specific IgE was determined in accordance with Ceska et al. [(33) Ceska, M. and Lundkvist, U. (1972). A new and simple radioimmunoassay method for the determination of IgE. Immunochemistry 9, 1021-1030], by coupling the natural and recombinant proteins (50 µg/ml) as well as the *P. judaica* extract (2 mg/ml) to discs activated with cyanogen bromide. 50 µl of serum from the patients was subsequently added and was incubated for 1 hour at ambient temperature. After washing the discs were incubated for 30 min at 37° C. with 50 µl of human anti IgE antibody bound to alkaline phosphatase, and quantification was carried out by following the instructions provided with the IgE specific HYTEC kit EIA by the manufacturer (Hycor Biomedical Inc.).

Figure 15:
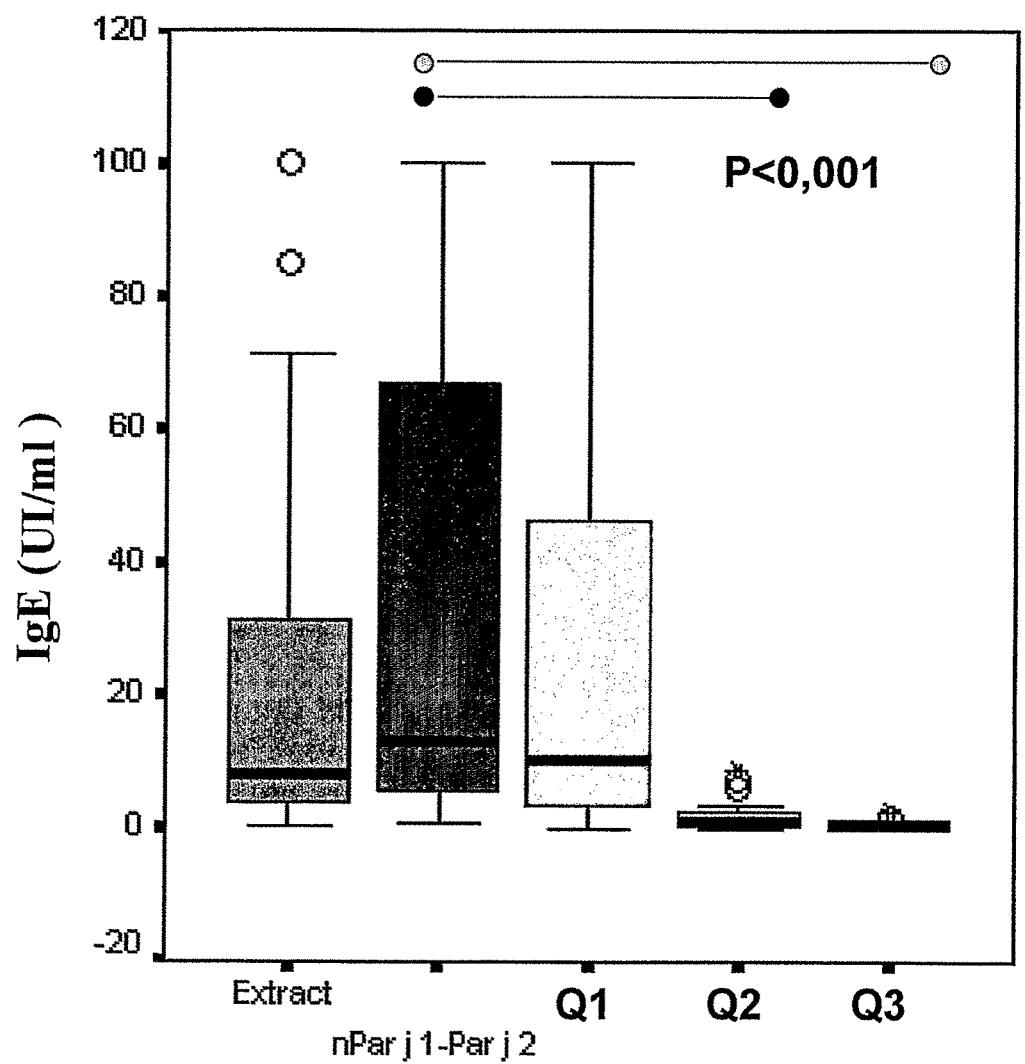
FIG. 15 shows the determination of specific IgE carried out with extract of *P. judaica*, nPar j 1-Par j 2, and Q1 (50 µg/ml), and Q2 and Q3 (250 µg/ml).

The results obtained merely reaffirm those obtained in vivo; of the three chimeras, Q1 maintained its immunogenic capacity relative to nPar j 1-Par j 2 whereas Q2 and Q3 had a very pronounced reduction in said capacity (P<0.001) (FIG. 15).

EXAMPLE 7

Induced Lymphoproliferation Experiments to Demonstrate the Immunogenic Capacity of the Chimeric Proteins Q1, Q2 and Q3

An essential requirement for the use of a hypoallergenic molecule in immunotherapy is the maintenance of its antigenicity (T epitopes). Therefore, to check whether, in addition to not binding IgE antibodies, our proteins remain antigenic, a lymphoproliferation test was carried out on mononuclear peripheral blood cells (CMSP) stimulated by the various proteins used in the experiments. The tests were carried out by a colorimetric method based on digestion of the tetrazole salt WST-1 by the mitochondrial dehydrogenases of viable cells to give rise to the formazan compound which is measured by colorimetry.

The CMSPs of 13 patients allergic to *P. judaica* were isolated by centrifugation in a density gradient using a lymphocite separating solution (LYMPHOPREP, Nycomed). The CMSPs were then resuspended at $1 \times 10^6$ viable cells/ml in culture medium (serum free medium AIM V, Gibco) and their viability was tested with 0.25% of tripan blue in PBS (Sigma Chemical Co.). The CMSPs prepared with viability greater than 90% were immediately used for the in vitro proliferation tests as described by the manufacturer (cell proliferation agent WST-1, Roche Diagnostics). They were deposited in flat-bottomed microplates (NUNCLON, NUNC), $2 \times 10^5$ CMSP in a final volume of medium of 200 µl and measurements were taken in triplicate at 37° C. and 5% $CO_2$ humidified atmosphere with the *P. judaica* extract and the various proteins purified to a final concentration of 0.0005-0.005-0.05-0.5-5 µg/ml. Triplicate controls of unstimulated cultures were included in all cases. After 3 days, 20 µl of the cell proliferation agent WST-1 was added to all the cups, and incubated for 4 h. The formazan produced by the metabolically active cells was quantified by absorbency at 450 nm. The recombinant proteins used in the test were the three chimeras and rPar j 1 and rPar j 2 expressed in *E. coli*.

In a first step, immunuogenic protein was scanned to determine the optimum concentration for subsequent development of the test. In all cases it was found that the protein concentration demonstrating maximum proliferation (IE %) was 0.5 µg/ml (FIG. 16).

Figure 17:
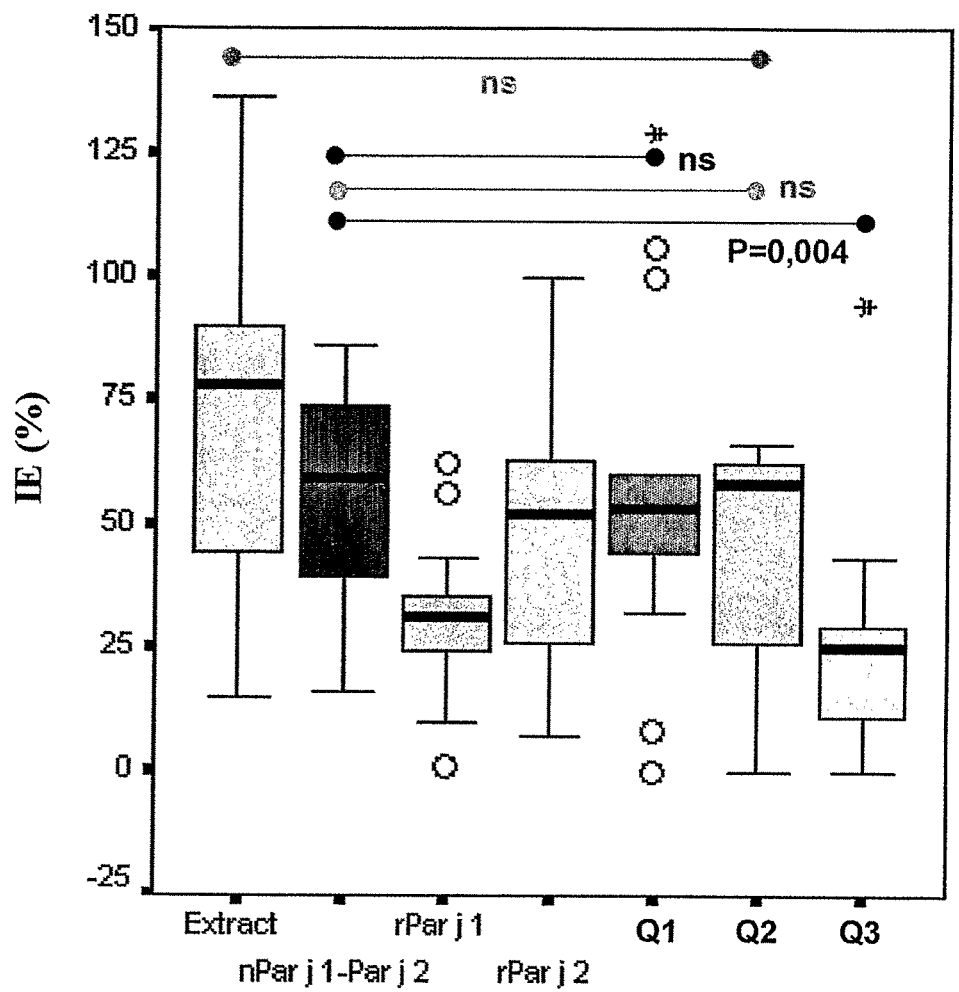
FIG. 17 shows the proliferation of T lymphocytes obtained with *P. judaica* extract and 0.5 Φg/ml of the three chimeric proteins and natural and recombinant forms of Par j 1 and Par j 2. The value shown is that of the stimulation index (%). No significant difference (ns).

The results of proliferation with the 13 patients allergic to *P. judaica* were determined by block diagram statistical analysis and non-parametric tests for two paired samples. The statistical analysis showed that the *P. judaica* extract used as a control had an antigenic stimulation capacity which did not differ greatly from that of nPar j 1-Par j 2 (P=0.142), and that Q1 and Q2 demonstrated a distribution of values which were not significantly different from those of the extract (P=0.152 and P=0.294 respectively) and nPar j 1-Par j 2 (P=0.484 and P=0.182 respectively) (FIG. 17). Q3 on the other hand barely had a stimulation capacity with respect to the extract (P=0.002) and nPar j 1-Par j 2 (P=0.004). On the other hand the greater antigenic power of rPar j 2 toward rPar j 1 against extract (P=0.142 and P=0.003 respectively) and nPar j 1-Par j 2 (P=0.041 and P=0.002 respectively) should be pointed out.

The results obtained show that Q2 still maintained said property, whereas Q3 comletely lost it. It can be concluded from all that has been stated about the process for obtaining different hypoallergenic molecules for treating the allergy to *P. judaica*, that the Q2 would be the candidate hypoallergenic molecule for developing satisfactory immunotherapy against the allergy to *P. judaica*.

Methods of Administration

The present invention relates to the use of the described hypoallergenic chimeras or synthetic peptides derived therefrom for hyposensitisation treatments in mammals. The method of hyposensitisation involves the repeated administration by parenteral (subcutaneous, intravenous or intramuscular), oral, sublingual, nasal or rectal routes of the allergen in question. These (poly)peptides can be administered alone and in combination with other pharmaceutically acceptable diluents and excipients, in accordance with the legislation in force and the galenical procedure for use.

REFERENCES

1. Miyamoto, T. (1992). Increased prevalence of pollen allergy in Japan. In Advances in Allergology and Clinical Immunology. P. Godard, J. Bousquet, and F. B. Michel, eds. (Comforth, U K: The Parthenon Publishing Group), pp. 343-347.
2. Akdis, C. A. Blaser, K. (2000). Mechanisms of allergen-specific immunotherapy. Allergy 55, 518-524.
3. Akdis, C. A., Joss, A., Akdis, M., and Blaser, K. (2001). Mechanism of IL-10 induced cell inactivation in allergic inflammation and normal response to allergens. Int. Arch Allergy Immunol. 124, 180-182.
4. Moverate, R. (2003). Immunological mechanisms of specific immunotherapy with pollen vaccines: implications for diagnostics and the development of improved vaccination strategies. Expert Rev. Vacc. 2, 85-97.
5. Wachholz, P. A., Soni, N. K., Till, S., and Durham, S. R. (2003). Inhibition of allergen-IgE binding to B cells by IgG antibodies after grass pollen immunotherapy. J. Allergy Clin. Immunol. 112; 915-922.
6. Valenta, R. and Linhart, B. (2005). Molecular design of allergy vaccines. Curr. Opin. Immunol. 17, 1-10.
7. Niederberger, V., Horak, F., Vrtala, S., Spitzauer, S., Krauth, M. T., Valent, P., Reisinger, J., Pelzmann, M., Hayek, B., Kronqvist, M., Gafvelin, G., Gronlund, H., Purohit, A., Suck, R., Fiebig, H., Cromwell, O., Pauli, G., van Hage-Hamsten, M., and Valenta, R. (2004). Vaccination with genetically engineered allergens prevents progression of allergic disease. Proc. Natl. Acad. Sci. U.S.A. 101, 14677-14682.
8. Schmid-Grendelmeier, P., Karamloo, F., Müller, U., Housley-Marcovic, Z., Soldatova, L., Zumkehr, J., Kemeny, D. M., Kündig, T., Reimers, A., von Beust, B. R., Salagianni, M., Akdis, M., Kussebi, F., Spangfort, M. D., Blaser, K., and Akdis, C. A. (2005). Prevention of allergy by a recombinant multi-allergen vaccine with reduced IgE binding and preserved T cell epitopes. Eur. J. Immunol. 35, 3268-3276.
9. Allam, J. P., Novak, N., Fuchs, C., Asen, S., Berge, S., Appel, T., et al. (2003) Characterization of dendritic cells from human oral mucosa: a new Langerhans' cell type with high constitutive FcεRI expression. J. Allergy Clin. Immunol. 112, 141-8.
10. von Bubnoff, D., Matz, H., Frahnert, C., Rao, M. L., Hanau, D., de la Salle, H., Bieber, T. (2003) FcεRI induces the triptophan degradation pathway involved in regulating T cell responses. J. Immunol. 169, 1810-1816.
11. Batard, T., Didierlaurent, A., Chabre, H., Mothes, N., Bussieres, L., Bohle, B., et al. (2005) Characterization of wild-type recombinant Bet v 1a as a candidate vaccine against birch pollen allergy. Int. Arch. Allergy Immunol. 136, 239-249.
12. Jutel, M., Jaeger, L., Suck, R., Meyer, H., Fiebig, H., Cromwell, O. (2005) Allergen-specific immunotherapy with recombinant grass pollen allergens. J. Allergy Clin. Immunol. 116, 608-13.
13. Niederberger, V., Horak, F., Vrtala, S., Spitzauer, S., Krauth, M. T., Valent, P., et al. (2004) Vaccination with genetically engineered allergens prevents progression of allergic disease. Proc. Natl. Acad. Sci. U.S.A. 101, 14677-82.
14. Cromwell, O., Fiebig, H., Suck, R., Kahlert, H., Nandy, A., Kettner, J., et al. (2006) Strategies for recombinant allergen vaccines and fruitful results from first clinical studies. Immunol. Allergy Clin. N. Am. 26, 261-81.
15. Colombo, P., Duro, G., Costa, M. A., Izzo, V., Mirisola, M., Locorotondo, G., Cocchiara, R., and Geraci, D. (1998). An update on allergens. *Parietaria* pollen allergens. Allergy 53, 917-921.
16. Colombo, P., Bonura, A., Costa, M., Izzo, V., Passantino, R., Licorotondo, G., Amoroso, S., and Gerasi, D. (2003). The allergens of *Parietaria*. Int. Arch. Allergy Immunol. 130, 173-179.
17. Carreira, J. and Polo, F. (1995). The allergens of *Olea europaea* and *Parietaria* spp. and their relevance in the Mediterranean Area. Allergy Clin. Immunol. News 7, 79-84.
18. Ayuso, R., Carreira, J., Lombardero, M., Duffort, O., Peris, A., Basomba, A., and Polo, F. (1993). Isolation by mAb based affinity chromatography of two Par j isoallergens. Comparison of their physicochemical, immunochemical and allergenic properties. Mol. Immunol. 30, 1347-1354.
19. Polo, F., Ayuso, R., and Carreira, J. (1990). HPLC purification of the main allergen of *Parieteria judaica* pollen. Mol. Immunol. 27, 151-157.
20. Polo, F., Ayuso, R., and Carreira, J. (1991). Studies on the relationship between structure and IgE-binding ability of *Parieteria judaica* allergen I. Mol. Immunol. 28, 169-175.
21. Duro, G., Colombo, P., Costa, M. A., Izzo, V., Porcasi, R., DiFiore, R., Locorotondo, G., Mirisola, M. G., Cocchiara, R., and Geraci, D. (1996). cDNA cloning, sequence analysis and allergological characterization of Par j 2.0101, a new major allergen of the Parietariajudaica pollen. FEBS Lett. 399, 295-298.
22. Costa, M. A., Colombo, P., Izzo, V., Kennedy, H., Venturella, S., Cocchiara, R., Mistrello, G., Falagiani, P., and Geraci, D. (1994). cDNA cloning expression and primary structure of Par j 1, a major allergen of *Parietaria judaica* pollen. FEBS Lett. 341, 182-186.
23. Amoresano, A., Pucci, P., Duro, G., Colombo, P., Costa, M. A., Izzo, V., Lambda, D., and Geraci, D. (2003). Assignment of disulphide bridges in Par j 2.0101, a major allergen of *Parietaria judaica* pollen. Biol. Chem. 384, 1165-1172.
24. Asturias, J. A., Gómez-Bayón, N., Eseverri, J. L., and Martinez, A. (2003). Par j 1 and Par j 2, the major allergens from *Parietaria judaica* pollen, have similar immunoglobulin E epitopes. Clinical and Experimental Allergy 33, 518-524.
25. van Ree, R. (2002). Clinical importance of non-specific lipid transfer proteins as food allergens. Biochem. Soc. Trans 30, 910-913.
26. Beezhold, D. H., Hickey, V. L., Kostyal, D. A., and et al. (2003). Lipid transfer protein from *Hevea brasiliensis* (Hev b 12), a cross-reactive latex protein. Ann Allergy Asthma Immunol 439-445.
27. Diaz-Perales, A., Lombardero, M., Sanchez-Monge, R., and et al. (2000). Lipid-transfer proteins as potential plant panallergens: cross-reactivity among proteins of *Artemisia* pollen, Castanea nut and Rosaceae fruits, with different IgE-binding capacities. Clin Exp Allergy 1403-1410.
28. Tejera, M. L., Villalba, M., Batanero, E., and Rodriguez, R. (1999). Identification, isolation, and characterization of Ole e 7, a new allergen of olive tree pollen. J. Allergy Clin. Immunol. 797-802.
29. Rodriguez, R., Villalba, M., Batanero, E., and et al. (2002). Allergenic diversity of the olive pollen. Allergy 6-16.
30. Hanahan, D. (1983). Studies on transformation of *Escherichia coli* with plasmids. J. Mol. Biol. 166, 557-580.
31. Laemmli, U. K. (1970). Cleavage of structural proteins during the assambly of the head of bacteriophage $T_4$. Nature 277, 680-685.
32. Towbin, H., Staehelin, I., and Gordon, J. (1979). Electrophoretic transfer of proteins from polyacrylamide gels to nitrocellulose sheets: Procedure and some applications. Proc. Natl. Acad. Sci. USA 76, 4350-4354.
33. Ceska, M. and Lundkvist, U. (1972). A new and simple radioimmunoassay method for the determination of IgE. Immunochemistry 9, 1021-1030.

The invention claimed is:

1. A chimeric protein consisting of an amino acid sequence with homology of at least 70% with SEQ ID NO: 4.

2. A chimeric protein consisting of the amino acid sequence of SEQ ID NO: 4.

3. A method for treating an allergy to *Parietaria judaica* pollen comprising administering a therapeutically effective amount of the chimeric protein of claim 1 to a subject in need thereof.

4. A method of preparing a medicament for the treatment of an allergy to *Parietaria judaica* comprising combining a therapeutically effective amount of the chimeric protein of claim 1 with at least one pharmaceutically acceptable excipient.

5. A pharmaceutical composition comprising a therapeutically effective amount of to the chimeric protein of claim 1 and a pharmaceutically acceptable excipient.

6. A pharmaceutical composition comprising a therapeutically effective amount of the chimeric protein of claim 2 and a pharmaceutically acceptable excipient.

7. The chimeric protein of claim 1, having an amino acid sequence with homology of at least 80% with SEQ ID NO.:4.

8. The chimeric protein of claim 1, having an amino acid sequence with homology of at least 90% with SEQ ID NO.:4.

9. The pharmaceutical composition of claim 5, wherein the chimeric protein has an amino acid sequence with homology of at least 80% with SEQ ID NO.:4.

10. The pharmaceutical composition of claim 5, wherein the chimeric protein has an amino acid sequence with homology of at least 90% with SEQ ID NO.:4.

11. The method of claim 3, wherein the chimeric protein has an amino acid sequence with homology of at least 80% with SEQ ID NO.:4.

12. The method of claim 3, wherein the chimeric protein has an amino acid sequence with homology of at least 90% with SEQ ID NO.:4.

13. The method of claim 3, wherein the chimeric protein has the amino acid sequence of SEQ ID NO.:4.

14. The method of claim 4, wherein the chimeric protein has an amino acid sequence with homology of at least 80% with SEQ ID NO.:4.

15. The method of claim 4, wherein the chimeric protein has an amino acid sequence with homology of at least 90% with SEQ ID NO.:4.

16. The method of claim 4, wherein the chimeric protein has the amino acid sequence of SEQ ID NO.:4.

* * * * *

SEQUENCE LISTING

```
<160> NUMBER OF SEQ ID NOS: 21

<210> SEQ ID NO 1
<211> LENGTH: 768
<212> TYPE: DNA
<213> ORGANISM: Artificial Sequence
<220> FEATURE:
<223> OTHER INFORMATION: synthetic sequence

<400> SEQUENCE: 1
atgagaggat ctcaccatca ccatcaccat gggatcctgc aagaaacctg cgggactatg      60
gtgagagcgc tgatgccgtg cctgccgttc gtgcagggga aagagaaaga gccgtcaaag     120
gggtgctgca gcggcgccaa aagattggac ggggagacga agacggggcc gcagagggtg     180
cacgcttgtg agtgcatcca gaccgccatg aagacttatt ccgacatcga cgggaaactc     240
gtcagcgagg tccccaagca ctgcggcatc gttgacagca agctcccgcc cattgacgtc     300
aacatggact gcaagacact tggagtggtt cctcggcaac cccaacttcc agtctctctc     360
cgtcatggtc ccgtcacggg cccaagtgat cccgcccaca aagcacggtt ggagagaccc     420
cagattagag ttccgccccc cgcaccggaa aaagccgaat cgaggaggc ttgcgggaaa      480 gtggtgcagg atataatgcc gtgcctgcat ttcgtgaagg gggaggagaa ggagccgtcg     540
aaggagtgct gcagcggcac gaagaagctg agcgaggagg tgaagacgac ggagcagaag     600
agggaggcct gcaagtgcat agtgcgcgcc acgaagggca tctccggtat caaaaatgaa     660
cttgtcgccg aggtccccaa gaagtgcgat attaagacca ctctcccgcc catcaccgcc     720
gacttcgact gctccaagat ccaaagtact attttcagag gttactat                  768

<210> SEQ ID NO 2
<211> LENGTH: 256
<212> TYPE: PRT
<213> ORGANISM: Artificial Sequence
<220> FEATURE:
<223> OTHER INFORMATION: synthetic peptide

<400> SEQUENCE: 2

Met Arg Gly Ser His His His His His His Gly Ile Leu Gln Glu Thr
1               5                   10                  15

Cys Gly Thr Met Val Arg Ala Leu Met Pro Cys Leu Pro Phe Val Gln
                20                  25                  30

Gly Lys Glu Lys Glu Pro Ser Lys Gly Cys Cys Ser Gly Ala Lys Arg
            35                  40                  45

Leu Asp Gly Glu Thr Lys Thr Gly Pro Gln Arg Val His Ala Cys Glu
        50                  55                  60

Cys Ile Gln Thr Ala Met Lys Thr Tyr Ser Asp Ile Asp Gly Lys Leu
65                  70                  75                  80

Val Ser Glu Val Pro Lys His Cys Gly Ile Val Asp Ser Lys Leu Pro
```

```
                85                  90                  95
Pro Ile Asp Val Asn Met Asp Cys Lys Thr Leu Gly Val Val Pro Arg
                100                 105                 110

Gln Pro Gln Leu Pro Val Ser Leu Arg His Gly Pro Val Thr Gly Pro
            115                 120                 125

Ser Asp Pro Ala His Lys Ala Arg Leu Glu Arg Pro Gln Ile Arg Val
130                 135                 140

Pro Pro Pro Ala Pro Glu Lys Ala Glu Phe Glu Ala Cys Gly Lys
145                 150                 155                 160

Val Val Gln Asp Ile Met Pro Cys Leu His Phe Val Lys Gly Glu Glu
                165                 170                 175

Lys Glu Pro Ser Lys Glu Cys Cys Ser Gly Thr Lys Lys Leu Ser Glu
            180                 185                 190

Glu Val Lys Thr Thr Glu Gln Lys Arg Glu Ala Cys Lys Cys Ile Val
        195                 200                 205

Arg Ala Thr Lys Gly Ile Ser Gly Ile Lys Asn Glu Leu Val Ala Glu
            210                 215                 220

Val Pro Lys Lys Cys Asp Ile Lys Thr Thr Leu Pro Pro Ile Thr Ala
225                 230                 235                 240

Asp Phe Asp Cys Ser Lys Ile Gln Ser Thr Ile Phe Arg Gly Tyr Tyr
                245                 250                 255

<210> SEQ ID NO 3
<211> LENGTH: 636
<212> TYPE: DNA
<213> ORGANISM: Artificial Sequence
<220> FEATURE:
<223> OTHER INFORMATION: synthetic sequence

<400> SEQUENCE: 3
atgagaggat ctcaccatca ccatcaccat gggatcctgc aagaaacctg cgggactatg      60
gtgagagcgc tgatgccgtg cctgccgttc gtgcagggga agagaaaga gccgtcaaag     120 gggctgcaga tccagaccgc catgaagact tattccgaca tcgacgggaa actcgtcagc     180 gaggtccccca agcactgcgg catcgttgac agcaagctcc cgcccattga cgtcaacatg     240
gactgcaaga cacttggagt ggttcctcgg caaccccaac ttccagtctc tctccgtcat     300
ggtcccgtca cgggcccaag tgatcccgcc cacaaagcac ggttggagag accccagatt     360
agagttccgc cccccgcacc ggaaaaagcc gaattcgagg aggcttgcgg aaagtggtg     420 caggatataa tgccgtgcct gcatttcgtg aaggggagg agaaggagcc gtcgaaggag     480
gatatcatag tgcgcgccac gaagggcatc tccggtatca aaaatgaact tgtcgccgag     540
gtccccaaga agtgcgatat taagaccact ctcccgccca tcaccgccga cttcgactgc     600
tccaagatcc aaagtactat tttcagaggt tactat                              636

<210> SEQ ID NO 4
<211> LENGTH: 212
<212> TYPE: PRT
<213> ORGANISM: Artificial Sequence
<220> FEATURE:
<223> OTHER INFORMATION: synthetic peptide

<400> SEQUENCE: 4

Met Arg Gly Ser His His His His His His Gly Ile Leu Gln Glu Thr
1               5                   10                  15

Cys Gly Thr Met Val Arg Ala Leu Met Pro Cys Leu Pro Phe Val Gln
                20                  25                  30
```

```
Gly Lys Glu Lys Glu Pro Ser Lys Gly Leu Gln Ile Gln Thr Ala Met
        35                  40                  45

Lys Thr Tyr Ser Asp Ile Asp Gly Lys Leu Val Ser Glu Val Pro Lys
    50                  55                  60

His Cys Gly Ile Val Asp Ser Lys Leu Pro Pro Ile Asp Val Asn Met
 65                  70                  75                  80

Asp Cys Lys Thr Leu Gly Val Val Pro Arg Gln Pro Gln Leu Pro Val
                85                  90                  95

Ser Leu Arg His Gly Pro Val Thr Gly Pro Ser Asp Pro Ala His Lys
            100                 105                 110

Ala Arg Leu Glu Arg Pro Gln Ile Arg Val Pro Pro Ala Pro Glu
        115                 120                 125

Lys Ala Glu Phe Glu Glu Ala Cys Gly Lys Val Val Gln Asp Ile Met
    130                 135                 140

Pro Cys Leu His Phe Val Lys Gly Glu Glu Lys Glu Pro Ser Lys Glu
145                 150                 155                 160

Asp Ile Ile Val Arg Ala Thr Lys Gly Ile Ser Gly Ile Lys Asn Glu
                165                 170                 175

Leu Val Ala Glu Val Pro Lys Lys Cys Asp Ile Lys Thr Thr Leu Pro
            180                 185                 190

Pro Ile Thr Ala Asp Phe Asp Cys Ser Lys Ile Gln Ser Thr Ile Phe
        195                 200                 205

Arg Gly Tyr Tyr
        210

<210> SEQ ID NO 5
<211> LENGTH: 600
<212> TYPE: DNA
<213> ORGANISM: Artificial Sequence
<220> FEATURE:
<223> OTHER INFORMATION: synthetic sequence

<400> SEQUENCE: 5
atgagaggat ctcaccatca ccatcaccat gggatcctgc cagaaacctg cgggactatg      60
gtgagagcgc tgatgccgtg cctgccgttc gtgcagggga agagaaaga gccgtcaaag     120 gggctgcaga tccagaccgc catgaagact tattccgaca tcgacgggaa actcgtcagc    180
gaggtcagat ctagcaagct cccgcccatt gacgtcaaca tggactgcaa gacacttgga    240
gtggttcctc ggcaacccca acttccagtc tctctccgtc atggtcccgt cacgggccca    300
agtgatcccg cccacaaagc acggttggag agacccagaa ttagagttcc gcccccgca    360 ccggaaaaag ccgaattcga ggaggcttgc gggaaagtgg tgcaggatat aatgccgtgc    420
ctgcatttcg tgaagggga ggagaaggag ccgtcgaagg aggatatcat agtgcgcgcc    480
acgaagggca tctccggtat caaaaatgaa cttgtcgccg aggtccccgg taccctcccg    540
cccatcaccg ccgacttcga ctgctccaag atccaaagta ctattttcag aggttactat    600

<210> SEQ ID NO 6
<211> LENGTH: 200
<212> TYPE: PRT
<213> ORGANISM: Artificial Sequence
<220> FEATURE:
<223> OTHER INFORMATION: synthetic peptide

<400> SEQUENCE: 6

Met Arg Gly Ser His His His His His His Gly Ile Leu Pro Glu Thr
 1               5                  10                  15

Cys Gly Thr Met Val Arg Ala Leu Met Pro Cys Leu Pro Phe Val Gln
```

```
            20                  25                  30
Gly Lys Glu Lys Glu Pro Ser Lys Gly Leu Gln Ile Gln Thr Ala Met
        35                  40                  45

Lys Thr Tyr Ser Asp Ile Asp Gly Lys Leu Val Ser Glu Val Arg Ser
    50                  55                  60

Ser Lys Leu Pro Pro Ile Asp Val Asn Met Asp Cys Lys Thr Leu Gly
65                  70                  75                  80

Val Val Pro Arg Gln Pro Gln Leu Pro Val Ser Leu Arg His Gly Pro
                85                  90                  95

Val Thr Gly Pro Ser Asp Pro Ala His Lys Ala Arg Leu Glu Arg Pro
            100                 105                 110

Gln Ile Arg Val Pro Pro Ala Pro Glu Lys Ala Glu Phe Glu Glu
        115                 120                 125

Ala Cys Gly Lys Val Val Gln Asp Ile Met Pro Cys Leu His Phe Val
    130                 135                 140

Lys Gly Glu Glu Lys Glu Pro Ser Lys Glu Asp Ile Ile Val Arg Ala
145                 150                 155                 160

Thr Lys Gly Ile Ser Gly Ile Lys Asn Glu Leu Val Ala Glu Val Pro
                165                 170                 175

Gly Thr Leu Pro Pro Ile Thr Ala Asp Phe Asp Cys Ser Lys Ile Gln
            180                 185                 190

Ser Thr Ile Phe Arg Gly Tyr Tyr
        195                 200

<210> SEQ ID NO 7
<211> LENGTH: 24
<212> TYPE: DNA
<213> ORGANISM: Artificial Sequence
<220> FEATURE:
<223> OTHER INFORMATION: synthetic sequence

<400> SEQUENCE: 7
cgggatcctg caagaaacct gcgg                                          24

<210> SEQ ID NO 8
<211> LENGTH: 25
<212> TYPE: DNA
<213> ORGANISM: Artificial Sequence
<220> FEATURE:
<223> OTHER INFORMATION: synthetic sequence

<400> SEQUENCE: 8
cggaattcgg cttttttccgg tgcgg                                        25

<210> SEQ ID NO 9
<211> LENGTH: 24
<212> TYPE: DNA
<213> ORGANISM: Artificial Sequence
<220> FEATURE:
<223> OTHER INFORMATION: synthetic sequence

<400> SEQUENCE: 9
cggaattcga ggaggcttgc ggga                                          24

<210> SEQ ID NO 10
<211> LENGTH: 25
<212> TYPE: DNA
<213> ORGANISM: Artificial Sequence
<220> FEATURE:
<223> OTHER INFORMATION: synthetic sequence

<400> SEQUENCE: 10
```
cgaagcttct aatagtaacc tctga                                         25

<210> SEQ ID NO 11
<211> LENGTH: 25
<212> TYPE: DNA
<213> ORGANISM: Artificial Sequence
<220> FEATURE:
<223> OTHER INFORMATION: synthetic sequence

<400> SEQUENCE: 11
cgctgcagcc cctttgacgg ctctt                                         25

<210> SEQ ID NO 12
<211> LENGTH: 25
<212> TYPE: DNA
<213> ORGANISM: Artificial Sequence
<220> FEATURE:
<223> OTHER INFORMATION: synthetic sequence

<400> SEQUENCE: 12
cgctgcagat ccagaccgcc atgaa                                         25

<210> SEQ ID NO 13
<211> LENGTH: 26
<212> TYPE: DNA
<213> ORGANISM: Artificial Sequence
<220> FEATURE:
<223> OTHER INFORMATION: synthetic sequence

<400> SEQUENCE: 13
cggaattcgg cttttccgg tgcggg                                         26

<210> SEQ ID NO 14
<211> LENGTH: 25
<212> TYPE: DNA
<213> ORGANISM: Artificial Sequence
<220> FEATURE:
<223> OTHER INFORMATION: synthetic sequence

<400> SEQUENCE: 14
cggaattcga ggaggcttgc gggaa                                         25

<210> SEQ ID NO 15
<211> LENGTH: 26
<212> TYPE: DNA
<213> ORGANISM: Artificial Sequence
<220> FEATURE:
<223> OTHER INFORMATION: synthetic sequence

<400> SEQUENCE: 15
cggatatcct ccttcgacgg ctcctt                                        26

<210> SEQ ID NO 16
<211> LENGTH: 25
<212> TYPE: DNA
<213> ORGANISM: Artificial Sequence
<220> FEATURE:
<223> OTHER INFORMATION: synthetic sequence

<400> SEQUENCE: 16
cggatatcat agtgcgcgcc acgaa                                         25

<210> SEQ ID NO 17
<211> LENGTH: 23
<212> TYPE: DNA
<213> ORGANISM: Artificial Sequence

```
<220> FEATURE:
<223> OTHER INFORMATION: synthetic sequence

<400> SEQUENCE: 17
cgagatctga cctcgctgac gag                                              23

<210> SEQ ID NO 18
<211> LENGTH: 23
<212> TYPE: DNA
<213> ORGANISM: Artificial Sequence
<220> FEATURE:
<223> OTHER INFORMATION: synthetic sequence

<400> SEQUENCE: 18
cgagatctag caagctcccg ccc                                              23

<210> SEQ ID NO 19
<211> LENGTH: 23
<212> TYPE: DNA
<213> ORGANISM: Artificial Sequence
<220> FEATURE:
<223> OTHER INFORMATION: synthetic sequence

<400> SEQUENCE: 19
cgggtaccgg ggacctcggc gac                                              23

<210> SEQ ID NO 20
<211> LENGTH: 23
<212> TYPE: DNA
<213> ORGANISM: Artificial Sequence
<220> FEATURE:
<223> OTHER INFORMATION: synthetic sequence

<400> SEQUENCE: 20
cgggtaccct cccgcccatc acc                                              23

<210> SEQ ID NO 21
<211> LENGTH: 21
<212> TYPE: DNA
<213> ORGANISM: Artificial Sequence
<220> FEATURE:
<223> OTHER INFORMATION: synthetic sequence

<400> SEQUENCE: 21
tttaaaaagg ccgtaatatc c                                                21
```